US010307755B1

(12) United States Patent
Bradley et al.

(10) Patent No.: US 10,307,755 B1
(45) Date of Patent: Jun. 4, 2019

(54) APPARATUSES AND METHODS FOR SAMPLE-SPECIFIC SELF-CONFIGURATION

(71) Applicant: BioCeryx Inc., Menlo Park, CA (US)

(72) Inventors: Kirk Bradley, Menlo Park, CA (US); David Devine, Menlo Park, CA (US); Andrew Sparks, Menlo Park, CA (US); Janice Li, Menlo Park, CA (US); Thomas Musci, Redwood City, CA (US); Robert Balog, Sunnyvale, CA (US)

(73) Assignee: BioCeryx Inc., Menlo Park, CA (US)

( * ) Notice: Subject to any disclaimer, the term of this patent is extended or adjusted under 35 U.S.C. 154(b) by 0 days.

(21) Appl. No.: 16/039,969

(22) Filed: Jul. 19, 2018

(51) Int. Cl.
*B01L 3/00* (2006.01)
*G01N 35/00* (2006.01)
*G01N 21/64* (2006.01)

(52) U.S. Cl.
CPC .. B01L 3/502715 (2013.01); G01N 35/00732 (2013.01); *B01L 2200/027* (2013.01); *B01L 2200/10* (2013.01); *B01L 2300/0861* (2013.01); *G01N 21/6428* (2013.01)

(58) Field of Classification Search
CPC ......... B01L 3/502715; B01L 2200/027; B01L 2200/10; B01L 2300/0861; G01N 35/00732; G01N 21/6428
See application file for complete search history.

(56) References Cited

U.S. PATENT DOCUMENTS

| 2012/0266986 | A1* | 10/2012 | Wimberger-Friedl ...................... B01L 3/502715 137/565.01 |
| 2014/0157915 | A1* | 6/2014 | Gross ..................... F16M 13/00 73/864.01 |
| 2016/0320375 | A1* | 11/2016 | Horii ................... B01F 13/0818 |
| 2017/0030859 | A1 | 2/2017 | Huber |
| 2018/0095100 | A1* | 4/2018 | Nguyen ............ B01L 3/502715 |
| 2018/0156734 | A1* | 6/2018 | Blanch .................. G01J 3/0262 |
| 2018/0221878 | A1* | 8/2018 | Tagawa ................ C12Q 1/6851 |

FOREIGN PATENT DOCUMENTS

WO    2017165817 A1    3/2017

* cited by examiner

*Primary Examiner* — Benjamin R Whatley
(74) *Attorney, Agent, or Firm* — Crawford Maunu PLLC

(57) ABSTRACT

Embodiments in accordance with the present disclosure are directed to configuring an analyzer apparatus for processing a particular sample-processing cartridge. The analyzer apparatus includes a portable container and sample-specific configuration circuitry. The portable container supports and integrates a sample-processing cartridge and the sample-specific configuration circuitry. The sample-specific configuration circuitry identifies configuration information specific to the sample-processing cartridge and configures the analyzer apparatus for a series of state configurations. The configuration can be performed by selecting which of a plurality of biological-sample stimulators to interact with the biological sample, identifying positions in the portable container for each of the selected ones of the plurality of biological-sample stimulators at different times, and while the selected ones of the plurality of biological-sample stimulators are in the identified positions, causing the interactions between the selected ones of the plurality of biological-sample stimulators and the biological sample.

19 Claims, 20 Drawing Sheets

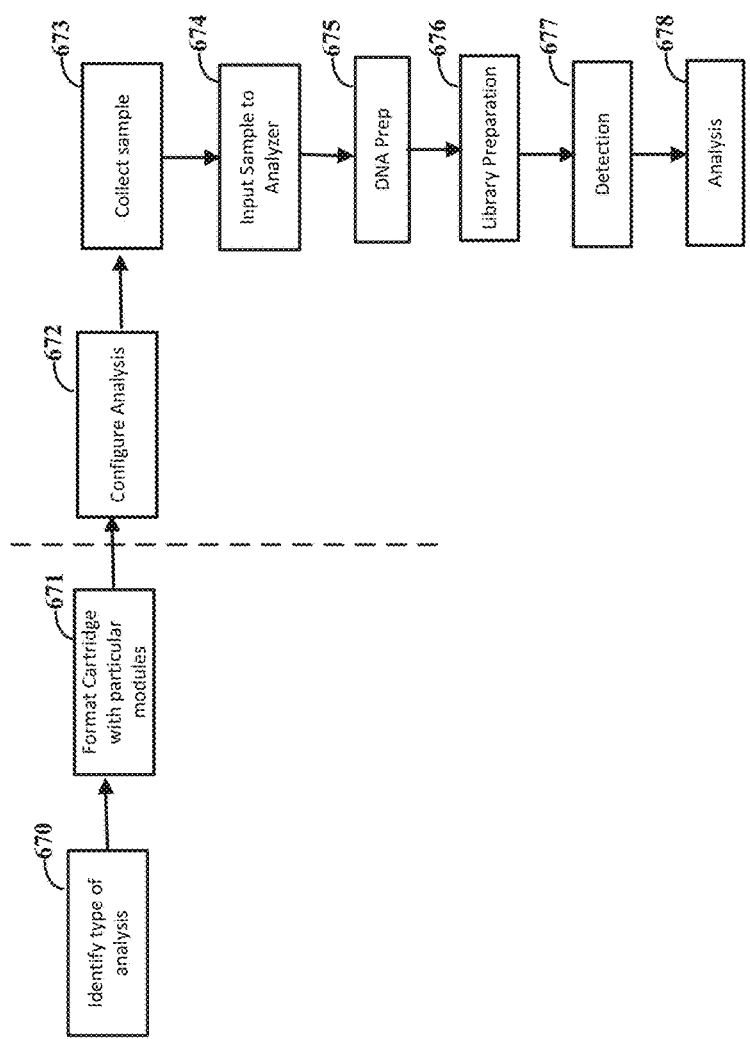

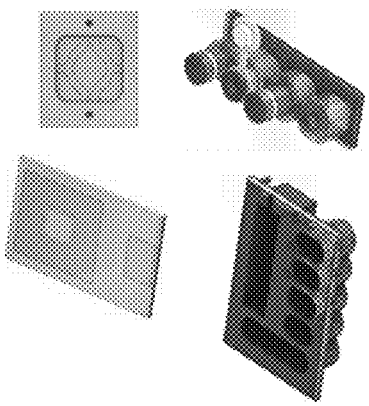
FIG. 8C
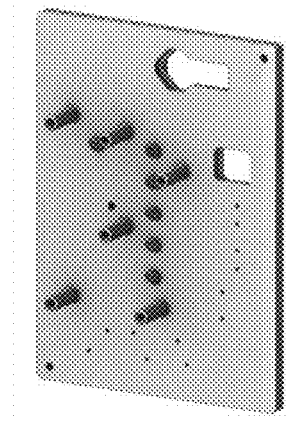
FIG. 8B
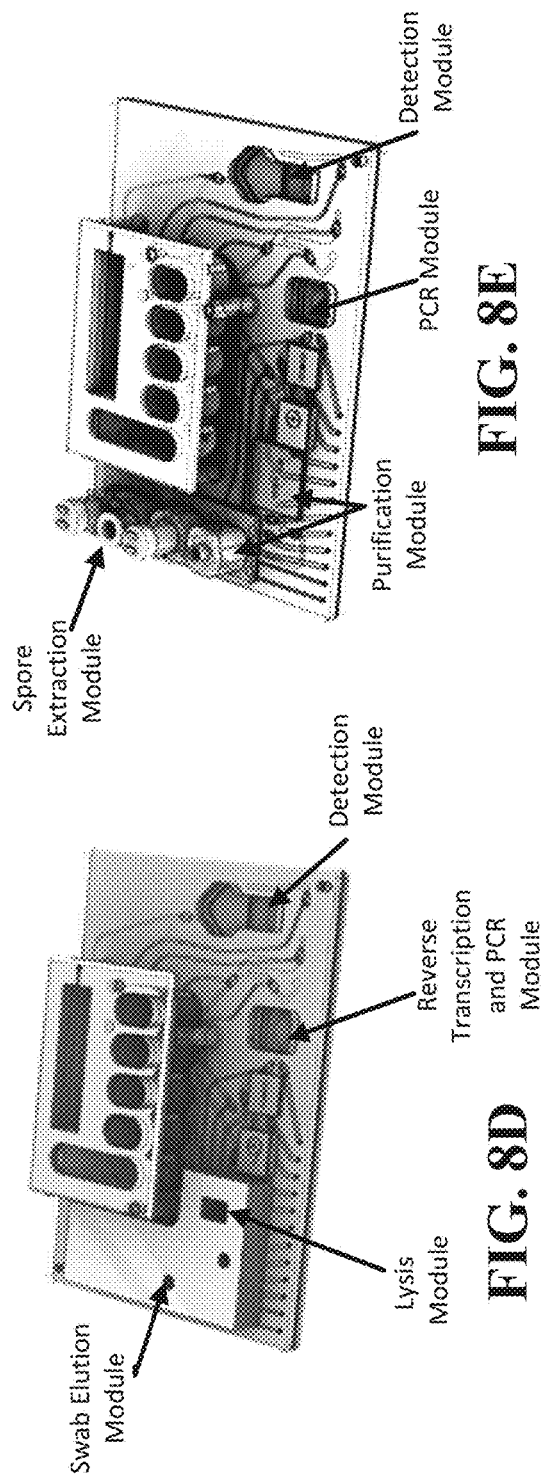
FIG. 8E
FIG. 8D

APPARATUSES AND METHODS FOR SAMPLE-SPECIFIC SELF-CONFIGURATION

OVERVIEW

Various embodiments in accordance with the present disclosure are directed to sample-specific self-configuration of an analyzer apparatus. In specific embodiments, the analyzer apparatus self-configures itself for processing many different sample-processing cartridges, having different configurations including different biochemical processes, different orders, and/or locations of the biochemical processes, and different parameters for performing the respective biochemical processes.

It can be advantageous for diagnosis of diseases or physiological conditions, as well as other analytic purposes, to analyze a biological sample to inform clinical decision making. Different types of biological samples and/or analysis use different biochemical processes, different orders of biochemical processes, and/or involve different parameters. Sample-processing cartridges, such as microfluidic chips, are used for processing the biological sample and include different biochemical processing modules and at different locations depending on the particular biochemical processes to be performed. In accordance with various embodiments, an analyzer apparatus is self-configurable for a plurality of different types of biological samples, and which allows for the analyzer apparatus to be used for a variety of different analyses and processes. The analyzer apparatus is flexible in a distributed setting that allows for the variety of analyses, while mitigating manual configuration by a user, such as a laboratory technician. The self-configurability of the analyzer apparatus allows for different diagnostic and/or processing workflows to be operated by minimally trained users at the point of biological specimen collection from a patient. For example, the self-configuration allows for processing different subsets of biological processes and different orders of biological processes from sample to sample. In specific embodiments, a single analyzer apparatus is used to perform genomic deoxyribonucleic acid (DNA) diagnostics, cell free DNA (cfDNA) diagnostics, messenger ribonucleic acid (mRNA) diagnostics, microRNA (miRNA) diagnostics, and other nucleic acid based tests. In some specific implementations, non-nucleic acid tests are converted to a nucleic acid readout and analyzed. For example, synthetic DNA coupled to an antibody is used as a readout for antibody protein interactions.

In a number of embodiments, the analyzer apparatus includes a portable container and sample-specific configuration circuitry. The portable container supports and integrates (removably) the sample-processing cartridge and the sample-specific configuration circuitry. The sample-processing cartridge includes a board assembly with fluid chambers and channels for processing a biological sample therein. The sample-specific configuration circuitry causes interactions with the biological sample. For example, the sample-specific configuration circuitry (or another component of the analyzer apparatus) includes a memory circuit used to store and access configuration information specific to the sample-processing cartridge and a configuration processing circuit used to configure the analyzer apparatus for a series of state configurations. The configuration information can be accessed and/or stored in the memory circuit internal to the analyzer apparatus prior to processing (or starting the process thereof) the biological sample. In other specific embodiments, the analyzer apparatus can access and/or store the configuration information during the analysis, such as in a step-by-step download process (e.g., on-the-fly and during the processing), as further described herein.

Configuring the analyzer apparatus for the series of state configurations, in accordance with various embodiments, includes selecting which of a plurality of biological-sample stimulators to interact with the biological sample, and identifying positions in the portable container for each of the selected ones of the plurality of biological-sample stimulators at different times. Configuring the analyzer apparatus for the series of state configurations further includes, while the each of the selected ones of the plurality of biological-sample stimulators are in the identified positions at the different times, causing the interactions between the selected ones of the plurality of biological-sample stimulators and the biological sample. For example, the analyzer apparatus can include the plurality of biological-sample stimulators. Each of the plurality of biological-sample stimulators includes or is an energy emitter that provides at least one type of energy output and transmits the energy output toward the biological sample, thereby causing the interaction with the biological sample. Example energy outputs includes electrical signals, optical signals, acoustic and/or ultrasound signals, thermal energy or transfer of thermal energy (e.g., heating and cooling), magnetic fields or energy, ionizing radiation, pressure, and other types of outputs.

The biological-sample stimulators include different hardware components. Example biological-sample stimulators include a pneumatic stimulator, a gantry (or other mechanical stimulator), an optical stimulator, a thermal energy tool, and an electrical stimulator. Although the various hardware components are described as "a stimulator," one or more of the stimulators, or components thereof, can be portions of another stimulator. In a number of specific embodiments, as further described herein, the biological-sample stimulators can include subassemblies of the analyzer apparatus. In specific embodiments, the pneumatic stimulator includes a pump, tubing and channels that sends forces toward the biological sample and thereby controls movement of the biological sample through the sample-processing cartridge. For example, the pneumatic stimulator constantly controls movement of the biological sample through the sample-processing cartridge based on the configuration information. In various instances during the analysis, the pneumatic stimulator can cause turbulence for mixing fluids together. The gantry selectively provides a plurality of interactions with the biological sample at a plurality of locations and based on the series of state configurations. In further specific aspects, gantry and a plurality of interface tools coupled to the gantry selectively output different types of energy outputs toward the biological sample to provide the different interactions with the biological sample at a plurality of locations across the analyzer apparatus, such as allowing for movement of interface tools to any location within the analyzer apparatus. Such interface tools can include a magnetic tool, a thermal energy tool, an acoustic tool, an optical tool, etc. A thermal energy tool includes a heat source and/or a cooling source and is used to transfer thermal energy from one medium to another for the purposes of heating and/or cooling. In some specific examples, the thermal energy tool is a radiator, a heat exchanger, and/or a heat sink, although embodiments are not so limited. As an example, the thermal energy tool outputs thermal energy toward the biological sample and thereby provides temperature control at specific locations and time. The thermal energy tool can be part of the gantry, in some specific aspects. The electrical stimulator, which includes circuitry, outputs timing signals for controlling actions performed by other of the plurality of biological-sample stimulators, such as controlling timing of the other biological-sample stimulators and processing image data of the biological sample to provide analytic results. In other specific aspects useful with the above-noted embodiments, the optical stimulator, which includes a light source and detector circuitry, outputs an optical signal toward the biological sample and captures image data of the biological sample responsive to the optical signal.

In specific embodiments, the sample-specific configuration circuitry further includes identification circuit. The identification circuit identifies the sample-processing cartridge using data located on the sample-processing cartridge and identifies the configuration information using the data. The data can include a barcode, such as a matrix bar code, a radio frequency tag, or a memory location, such as a cloud-based location or memory location internal to the analyzer apparatus. In some embodiments, the data includes the configuration information and/or can instruct how to obtain the configuration information. For example, the sample-specific configuration circuitry can include a communication circuit used to download the configuration information from the memory location. The configuration information is stored on a memory circuit of the sample-specific configuration circuitry (e.g., either prior to the identification or responsive to a download from an external memory location). In accordance with such specific embodiments, the configuration processing circuit processes the configuration information accessed from the memory circuit and provides the series of state configurations using the processed configuration information.

Configuring the analyzer apparatus for the series of state configurations can include providing spatial location information of specific biochemical processing modules self-contained in the sample-processing cartridge along with timing information and identification of the selected biological-sample stimulators used for performing the analysis and at the different times. In various specific aspects, the sample-specific configuration circuitry instructs the selected biological-sample stimulators to interface with specific biochemical processing modules of the sample-processing cartridge based on parameters identified by the configuration information. The parameters include spatial locations of the biochemical processing modules, the selected biological-sample stimulators used to interface with the biochemical processing modules, corresponding times for the interface, and interface parameters indicative of the interactions with the biological sample. In more-specific embodiments, the parameters include specific instructions for the biological-sample stimulators interfacing with the biochemical processing modules including time requirements of the interaction, two-dimensional or three-dimensional locations within the sample-processing cartridge for the interface, interface parameters indicative of the interactions with the biological sample, which are sometimes herein referred to as "interface parameters". Example interface parameters include exposure time, exposure laser power and duration, stringency temperature, movement of fluid in the sample-processing cartridge, temperature and duration of temperature at particular times, volumes delivered, pressure, flow rate, identification of selected biological-sample stimulators and the interactions, voltage and current requirements for required forces, laser power, and various combinations thereof.

Various aspects of the present disclosure are directed to methods of self-configuring an analyzer apparatus. For example, the analyzer apparatus in accordance with the above-noted embodiments is configured for performing a particular process on a biological sample. The method includes providing a sample-processing cartridge comprising a board assembly with fluid chambers, channels and a biological sample therein to a portable container of an analyzer apparatus. The method further includes using sample-specific configuration circuitry to identify configuration information specific to the sample-processing cartridge by scanning a location of the sample-processing cartridge for data indicative of the configuration information, and configuring the analyzer apparatus for a series of state configurations for performing the process on the biological sample using the configuration information. Configuring the analyzer apparatus for the series of state configurations includes selecting which of a plurality of biological-sample stimulators of the analyzer apparatus interact with the biological sample at different times specific to an analysis of the biological sample, identifying positions in the portable container for each of the selected ones of the plurality of biological-sample stimulators at the different times, and while the selected ones of the plurality of biological-sample stimulators are in the identified positions at the different times, causing interaction between the selected ones of the plurality of biological-sample stimulators and the biological sample.

Other example aspects are directed to a gantry apparatus that is configured to interact with a sample-processing cartridges containing a biological sample. The gantry apparatus includes a set of tracks, a bridge framework, and a gantry head. The set of tracks are arranged parallel to one another and elongates in a first direction. The bridge framework spans the set of tracks and is configured to travel along the set of tracks in the first direction. The gantry head is supported by bridge framework and is configured to travel in a second direction that is perpendicular to the first direction and along the bridge framework. The gantry head includes a plurality of interface tools arranged on the gantry head and that can be used to selectively provide the plurality of interactions with a biological sample at a plurality of locations. For example, the gantry head can physically move to different locations between and outside of the set of tracks in two-dimensional or three-dimensional directions.

In other specific aspects useful with the above-noted embodiments, the plurality of interface tools are located about or around the periphery of the gantry head. The gantry head can provide one of the plurality of interactions with the biological sample by rotating the gantry head to align a respective interface tool with a particular location of the plurality of locations. Example interface tools include a heat source and/or a cooling source to heat and/or cool the biological sample, a magnetic source to apply magnetic forces, an acoustic tool to apply acoustic forces, a motor, among various other interface tools. In various embodiments, the gantry head is detachable from the bridge framework. For example, the gantry head can be detached from the bridge framework and another gantry head, which may have a different set of interface tools, can be attached to the bridge framework.

Various related and specific aspects are directed to a sample-processing cartridge. In some specific embodiments, the analyzer apparatus includes the sample-processing cartridge. The sample-processing cartridge includes a plurality of biochemical processing modules and the data that provides the configuration information. The plurality of biochemical processing modules are self-contained in the board assembly and in fluidic communication with the fluid chambers and channels. As previously described, the data is located on the sample-processing cartridge which can provide or be used to provide the configuration information. For example, the configuration information is specific to the sample-processing cartridge and used for configuring an analyzer apparatus to perform the biochemical processing using the plurality of biochemical processing modules. The data can include a barcode, a radio frequency tag, and/or a cloud-based location or other memory location.

The above discussion is not intended to describe each embodiment or every implementation of the present disclosure. The figures and detailed description that follow also exemplify various embodiments.

BRIEF DESCRIPTION OF THE FIGURES

Various example embodiments may be more completely understood in consideration of the following detailed description in connection with the accompanying drawings in the Appendix, which form part of this patent document.

FIG. 6 illustrates another example method of self-configuring an analyzer apparatus in accordance with various embodiments of the present disclosure;

FIGS. 7A-7I illustrates an example gantry apparatus and/or an analyzer apparatus including a gantry in accordance with various embodiments of the present disclosure;

FIGS. 8A-8E illustrate examples of sample-processing cartridges, in accordance with various embodiments of the present disclosure;

Figure 1:
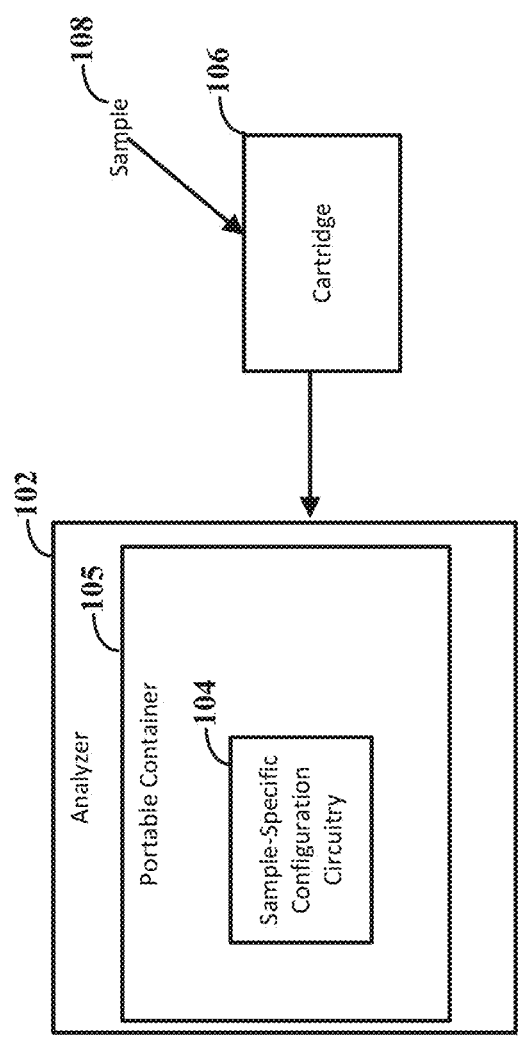
FIG. 1 illustrates an example of an analyzer apparatus in accordance with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Embodiments in accordance with the present disclosure are useful for self-configuring an analyzer apparatus for a sample-specific analysis or process. In specific aspects, the analyzer apparatus configures itself for processing a specific sample-processing cartridge, having biochemical processing modules at particular locations, based on configuration information identified using the sample-processing cartridge. The configuration information identifies a series of state configurations associated with a plurality of biological-sample stimulators of the analyzer apparatus used for performing an analysis on a biological sample within the sample-processing cartridge by causing interactions with the biological sample. While not necessarily so limited, various aspects of the disclosure may be appreciated through a discussion of examples in this regard.

Accordingly and in the following description, various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Embodiments in accordance with the present disclosure are directed to an analyzer apparatus that is self-configurable for a plurality of different types of biological samples, and which can allow for the analyzer apparatus to be used for a variety of different analyses. The analyzer apparatus is flexible in a distributed setting which allows for a variety of analyses while mitigating manual configuration by a user, such as a laboratory technician. A single analyzer apparatus can be used to perform a variety of processes and analyses on different sample-processing cartridges having different biochemical processing modules, at different locations and/or in different orders, and for processing different types of biological samples. The analyzer apparatus can self-configure while in the field (e.g., clinical setting) using configurable hardware that allows for many different combinations of biochemical processing in different combinations or orders, volumes, and/or spatial locations of the respective sample-processing cartridge. The analyzer apparatus can be used for providing distributed analysis, such as diagnostics, over a number of different class of applications, including, but not limited to, multiple different infectious disease test, genomic tests, and antibody protein interactions. As the analyzer apparatus self-configures, based on data located on the respective sample-processing cartridge, the apparatus can be used for a variety of different analysis workflows to be operated by a minimally trained user at the point of biological sample collection from a patient.

In a number of embodiments, the analyzer apparatus includes a portable container and sample-specific configuration circuitry. The portable container supports and integrates a sample-processing cartridge and the sample-specific configuration circuitry. The portable container can removably integrate different sample-processing cartridges, each including a board assembly with fluid chambers and channels for processing a biological sample therein. The sample-specific configuration circuitry can identify configuration information specific to a respective sample-processing cartridge and configures the analyzer apparatus for a series of state configurations for performing the process on the biological sample. For example, the sample-specific configuration circuitry includes a memory circuit and a processing circuit. The memory circuit stores and/or accesses configuration information specific to the sample-processing cartridge. The processing circuit configures the analyzer apparatus, using the configuration information, for a series of state configurations using the configuration information.

As further described herein, the configuration information can be located on the memory circuit internal to the analyzer apparatus, on an external memory circuit (and is downloaded and subsequently stored on the memory circuit of the analyzer apparatus) and/or on the sample-processing cartridge itself. The location can be identified using data located on the sample-processing cartridge. The configuration information is stored by the analyzer apparatus prior to performing or starting the process on the biological sample, in some embodiments. As a specific example, the processing circuit accesses the configuration information in a memory location of the memory circuit (internal to the analyzer apparatus) and then temporarily stores the configuration information for accessing during the process, such as cache memory and/or a volatile memory location. In another specific example, the processing circuit accesses the configuration information from an external location, such as the cloud, and then temporarily stores the configuration information for accessing during the process. Although embodiments are not limited to the above examples, and in some instances, the configuration information is not all accessed and/or internally stored prior to starting the process on the biological sample. In some embodiments, a portion of the configuration information is stored prior to starting the process, and remaining portion(s) are accessed and stored during the processing, such as downloading on-the-fly in which the configuration information for the next step in the process is accessed and saved while processing a previous step.

The sample-specific configuration circuitry, in a number of embodiments, includes identification circuit and the configuration processing circuit. The identification circuit identifies the sample-processing cartridge using data located on the sample-processing cartridge and identify the configuration information using the data. The data can include a barcode, such as a matrix barcode, a radio frequency tag, or a memory location (e.g., a memory location of the analyzer apparatus, an external circuitry memory location and/or a cloud-based location). In some specific embodiments, the sample-specific configuration circuitry includes a communication circuit used to download the configuration information from the memory location, such as the cloud-based location, the sample-processing cartridge, or the memory circuit internal to the analyzer apparatus. The configuration processing circuit further processes the configuration information accessed from the memory circuit and which provides the series of state configurations using the processed configuration information. In various embodiments, the sample-processing cartridge can, itself, include the configuration information. As a specific example, the configuration information is stored on a barcode (e.g., a QR code) and read by the identification circuit.

Configuring the analyzer apparatus for the series of state configurations includes using the configuration information to select which of a plurality of biological-sample stimulators to interact with the biological sample, and identify positions in the portable container for each of the selected ones of the plurality of biological-sample stimulators at different time. Additionally, the configuration of the series of state configurations further includes, while the each of the selected ones of the plurality of biological-sample stimulators are in the identified positions, causing the interactions at the different times, between the selected ones of the plurality of biological-sample stimulators and the biological sample. For example, the analyzer apparatus can include the plurality of biological-sample stimulators. Each of the plurality of biological-sample stimulators is or includes an energy emitter that provides at least one type of energy output and transmits the energy output toward the biological sample, thereby causing the interaction with the biological sample. Example energy outputs includes electrical signals, optical signals, thermal energy or transfer of thermal energy, sound waves (e.g., acoustic and/or ultrasound signals), magnetic fields, ionizing radiation, pressure, and other types of outputs.

Example biological-sample stimulators include a pneumatic stimulator, a gantry (or other mechanical stimulator), an optical stimulator, a thermal energy tool, and an electrical stimulator. Although the various hardware components are described as "a stimulator," one or more of the stimulators, or components thereof, can be portions of another stimulator. In a number of specific embodiments, as further described herein, the biological-sample stimulators can include subassemblies of the analyzer apparatus. In specific embodiments, the pneumatic stimulator includes a pump, tubing and channels, and sends forces toward the biological sample and thereby controls movement of the biological sample through the sample-processing cartridge. For example, the pneumatic stimulator constantly controls movement of the biological sample through the sample-processing cartridge based on the configuration information. In various instances during the analysis, the pneumatic stimulator can cause turbulence for mixing fluids together. In further specific aspects, a gantry and a plurality of interface tools coupled to the gantry selectively output different types of energy outputs toward the biological sample to provide different interactions with the biological sample at a plurality of locations across the analyzer apparatus, such as allowing for movement of interface tools to any location within the analyzer apparatus. A thermal energy tool, which includes a heat source and/or a cooling source, outputs thermal energy toward the biological sample or otherwise provides a transfer of thermal energy to or from the biological sample, and thereby provides temperature control at specific locations and time. The thermal energy tool can be part of the gantry, in some specific aspects. And, the electrical stimulator, which includes circuitry, outputs timing signals for controlling actions performed by other of the plurality of biological-sample stimulators, such as controlling timing of the other hardware components and processing image data of the biological sample to provide analytic results. In other specific aspects useful with the above-noted embodiments, the optical stimulator, which includes a light source and detector circuitry, outputs an optical signal toward the biological sample and captures image data of the biological sample responsive to the optical signal.

The biological-sample stimulators, in specific embodiments, are configured for the series of state configurations by the configuration information providing spatial location information of specific biochemical processing modules self-contained in the sample-processing cartridge along with timing information (e.g., the different times) and the identification of the selected biological-sample stimulators used for performing the analysis at the different times. The sample-specific configuration circuitry can instruct the selected biological-sample stimulators to interface with the specific biochemical processing modules of the sample-processing cartridge based on parameters identified by the configuration information, the parameters including spatial locations of the biochemical processing modules, the selected biological-sample stimulators used to interface with the biochemical processing modules, corresponding times for the interface, and interface parameters indicative of the interactions with the biological sample. In more specific embodiments, the parameters include specific instructions for the biological-sample stimulators interfacing with the biochemical processing modules including time requirements of the interaction, two-dimensional or three-dimensional locations within the sample-processing cartridge for the interface, and values of the interface that are indicative or associated with the interactions with the biological sample. Example interface parameters include exposure time, exposure laser power and duration, stringency temperature, movement of fluid in the sample-processing cartridge, temperature and duration of temperature at particular times, volumes delivered, pressure, flow rate, voltage and current requirements for required forces, laser power, and various combinations thereof used for processing the biological sample for a specific analysis within the sample-processing cartridge.

Various embodiments of the present disclosure are directed to methods of self-configuring an analyzer apparatus. For example, the analyzer apparatus, such as that described above, is configured for performing a particular process on a biological sample. The method can include providing a sample-processing cartridge comprising a board assembly with fluid chambers, channels and a biological sample therein to a portable container an analyzer apparatus. The method includes using sample-specific configuration circuitry to identify configuration information specific to the sample-processing cartridge by scanning a location of the sample-processing cartridge, and configuring the analyzer apparatus for a series of state configurations for performing the process on the biological sample using the configuration information. Configuring the analyzer apparatus for the series of state configurations includes selecting which of a plurality of biological-sample stimulators of the analyzer apparatus interact with the biological sample at the different times, identifying positions in the portable container for each of the selected ones of the plurality of biological-sample stimulators at the different times, and while the selected ones of the plurality of biological-sample stimulators are in the identified positions at the different times, causing the interactions between the selected ones of the plurality of biological-sample stimulators and the biological sample.

Other example embodiments are directed to a gantry apparatus that is configured to interact with a sample-processing cartridges containing a biological sample. For example, the above-described gantry can include a gantry apparatus having a plurality of interface tools. The gantry apparatus includes a set of tracks, a bridge framework, and a gantry head. The set of tracks are arranged parallel to one another and can elongate in a first direction. The bridge framework spans the set of tracks and is configured to travel along the set of tracks in the first direction. The gantry head is supported by bridge framework and is configured to travel in a second direction that is perpendicular to the first direction and along the bridge framework. The gantry head includes a plurality of interface tools arranged on the gantry head and that are used to selectively provide a plurality of interactions with a biological sample at a plurality of locations within the portable container. For example, the gantry head can physically move to different locations between and outside of the set of tracks in two-dimensional or three-dimensional directions to provide the plurality of interactions, which are identified via the configuration information.

The plurality of interface tools can be located about or around the periphery of the gantry head. In such embodiments, the gantry head provides one of the plurality of interactions with the biological sample by rotating the gantry head to align a respective interface tool with a particular location of the plurality of locations. Example interface tools include a heat source and/or a cooling source to heat and/or cool the biological sample, a magnetic source to apply magnetic forces, an acoustic tool to apply acoustic forces, a motor, among various other interface tools. In various embodiments, the gantry head is detachable from the bridge framework. For example, the gantry head can be detached from the bridge framework and another gantry head, which may have a different set of interface tools, can be attached to the bridge framework.

Various related embodiments are directed to the sample-processing cartridge. In some specific embodiments, the analyzer apparatus can include the sample-processing cartridge. The sample-processing cartridge can include a plurality of biochemical processing modules and the data that provides the configuration information. The plurality of biochemical processing modules are self-contained in the board assembly and in fluidic communication with the fluid chambers and channels. As previously described, the data is located on the sample-processing cartridge and used to provide the configuration information. The configuration information is specific to the sample-processing cartridge and used for configuring an analyzer apparatus to perform the biochemical processing using the plurality of biochemical processing modules. The data can include a barcode, a radio frequency tag, and/or a cloud-based location or other memory location.

The above-describes apparatus and methods can be used to self-configure an analyzer apparatus, while in the field, for a plurality of different types of biological samples, and which can allow for the analyzer apparatus to be used for a variety of different analysis. More specifically, the analyzer apparatus is configured to be flexible in a distributed setting that allows for the variety of analysis, while mitigating manual configuration by a user, such as a laboratory technician. The self-configurability of the analyzer apparatus allows for different diagnostic and/or processing workflows to be operated by minimally trained users at the point of biological specimen collection from a patient. The self-configuration can allow for different subsets of biological processes and different orders of biological processes from sample to sample. In specific embodiments, a single analyzer apparatus is used to perform genomic deoxyribonucleic acid (DNA) diagnostics, cell free DNA diagnostics, messenger ribonucleic acid (mRNA) diagnostics, microRNA (miRNA) diagnostics, and other nucleic acid based tests. In some instances, non-nucleic acid tests can be converted to a nucleic acid readout and analyzed. For example, synthetic DNA coupled to an antibody can be used as a readout for antibody protein interactions.

Turning now to the figures, FIG. 1 illustrates an example of an analyzer apparatus in accordance with various embodiments of the present disclosure. The analyzer apparatus 102 can include a portable container 105 and sample-specific configuration circuitry 104. The portable container 105 supports and integrates (e.g., accept and hold) a sample-processing cartridge 106 and also supports and integrates the sample-specific configuration circuitry 104. The sample-processing cartridge 106, as further illustrated herein, can include a board assembly with fluid chambers and channels for processing a biological sample 108 therein. The portable container 105 receives the sample-processing cartridge 106 and couples to one or more biochemical processing modules of the sample-processing cartridge 106. In specific embodiments, a cartridge assembly or another component can selectively cause fluidic connection between biochemical processing modules of the sample-processing cartridge 106. For example, the fluidic connection can occur in response to placing the sample-processing cartridge 106 in the portable container 105 and closing a top (e.g., a lid) of the analyzer apparatus 102, which may cause a biochemical processing module to be pierced (e.g., reagents module) and which results in a fluidic connection between two or more biochemical processing modules.

A variety of different analyses and processes can be performed on a biological sample or different biological samples using different sample-processing cartridges. For each respective analysis or process, a different sample-processing cartridge is used to perform different biochemical processes using different modules and locations of the modules. The analyzer apparatus 102 self-configures to process the different sample-processing cartridges using sample-specific configuration circuitry 104. The sample-specific configuration circuitry 104 identifies configuration information specific to the sample-processing cartridge 106 and uses the configuration information to configure the analyzer apparatus 102 for a series of state configurations for performing the process or analysis on the biological sample 108. The series of state configurations, as further described herein, can be associated with the positions of and interactions provided by different biological-sample stimulators that are integrated within and supported by the portable container 105.

The sample-specific configuration circuitry 104 includes a memory circuit and a configuration processing circuit. The memory circuit is used to store and access the configuration information specific to the sample-processing cartridge 106. The configuration processing circuit configures the analyzer apparatus for the series of state configurations using the configuration information. In specific embodiments, the sample-specific configuration circuitry 104 includes identification circuit. The identification circuit can identify the sample-processing cartridge 106 using data located on the sample-processing cartridge 106 and identify the configuration information using the data. The data can include a barcode on the sample-processing cartridge 106, data stored in a radio frequency tag on the sample-processing cartridge 106, and/or data identifying a memory locations and/or cloud-based location, among other data. In some embodiments, the analyzer apparatus 102 further includes a communication circuit used to download configuration information, such as from a memory location or cloud-based location identified using the sample-processing cartridge 106. In various embodiments, the configuration information is stored on the memory circuit of the sample-specific configuration circuitry 104, such as prior to the identification or responsive to a download from an external memory location.

In various specific embodiments, the configuration information is located on the sample-processing cartridge (e.g., it is the data), on external circuitry, and/or in a memory location internal to the analyzer apparatus (e.g., on the memory circuit). The location can be identified from or include the data on the sample-processing cartridge, which is identified by the identification circuit and/or used by the communication circuit to access and/or download the configuration information. In some embodiments, the configuration information is stored on the memory circuit prior to processing the sample-processing cartridge. For example, the configuration information can be temporarily stored in an easy to locate memory location, such as cache memory. In a specific embodiment, the analyzer apparatus accesses the configuration information in an internal memory location of the analyzer apparatus and then temporarily stores the configuration information in another location for accessing during the process, although embodiments are not so limited and the analyzer apparatus can access the configuration without storing in the second location. In another specific example, the analyzer apparatus accesses the configuration information from an external location, such as the cloud, and then internally stores the configuration information for accessing during the process. As may be appreciated, embodiments are not limited to the above examples, and in some instances, the configuration information is not all accessed and/or internally stored prior to starting the process on the biological sample. As an example, a portion of the configuration information is stored prior to starting the process, and remaining portion(s) are accessed and stored during the processing, such as downloading on-the-fly in which configuration information for the next step in the process is accessed and saved (temporarily or permanently) while processing the previous step.

Figure 2:
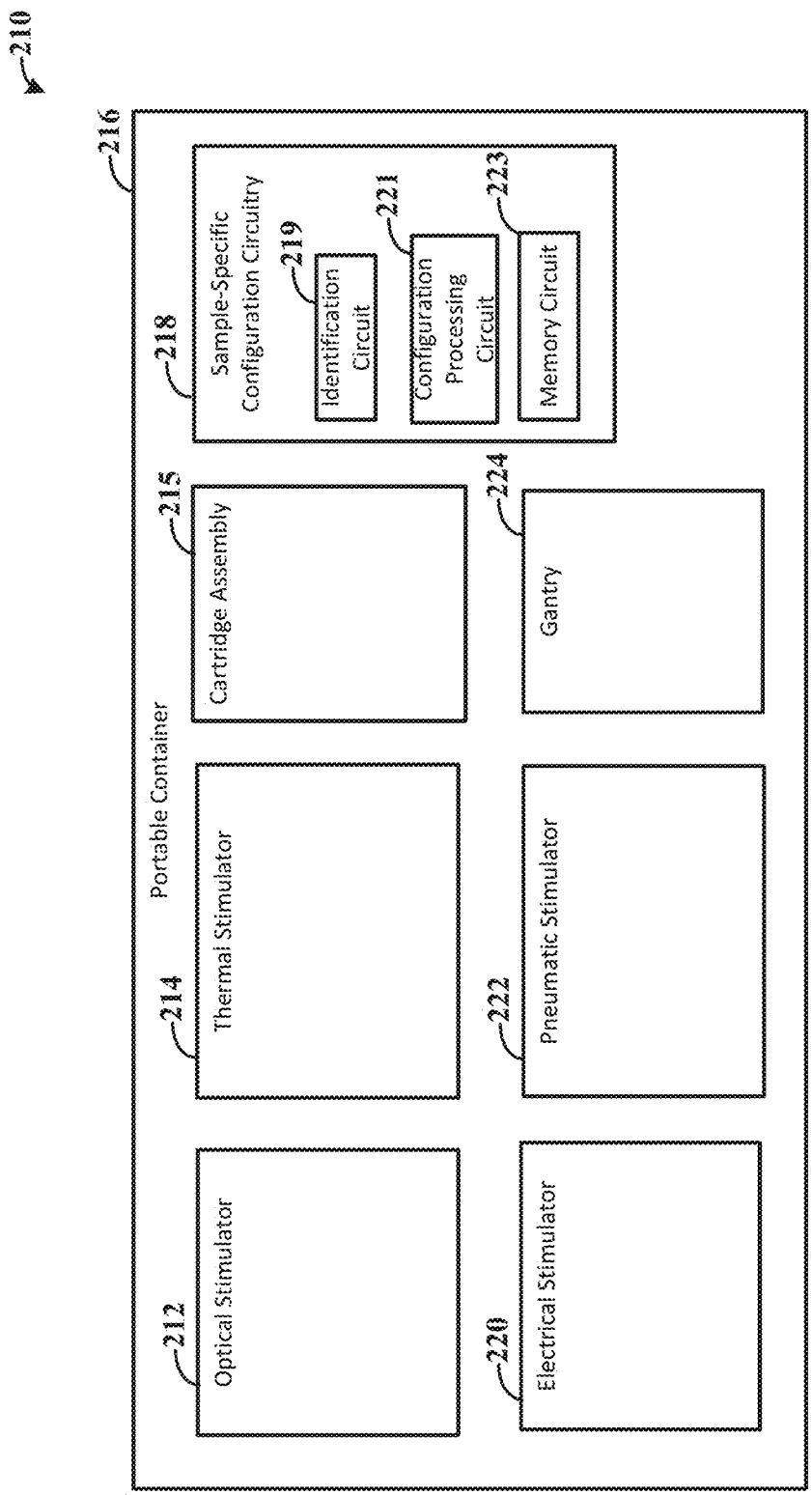
FIG. 2 illustrates an example of an analyzer apparatus in accordance with various embodiments of the present disclosure.

As further illustrated herein, such as by FIG. 2, the analyzer apparatus 102 includes plurality of biological-sample stimulators that interact physically with the biological sample. The biological-sample stimulators are or include emitters that provide at least one type of energy output and transmit the energy output toward the biological sample, thereby causing the interactions with the biological sample. Example energy outputs includes electrical signals, optical signals, thermal energy or transfer of thermal energy, sound waves (e.g., acoustic and/or ultrasound signals), magnetic fields, ionizing radiation, pressure, and other types of outputs.

The sample-specific configuration circuitry 104 can configure at least some of the plurality of biological-sample stimulators for the series of state configurations. Configuring the analyzer apparatus 102 for the series of state configurations, in accordance with various embodiments, includes using the configurations information to configure the analyzer apparatus 102 by selecting which of a plurality of biological-sample stimulators to interact with the biological sample at different times specific to an analysis of the biological sample, and identifying positions in the portable container for each of the selected ones of the plurality of biological-sample stimulators at the different times. Configuring the analyzer apparatus for the series of state configurations further includes, while the each of the selected ones of the plurality of biological-sample stimulators are in the identified positions at the different times, causing the interactions between the selected ones of the plurality of biological-sample stimulators and the biological sample.

Example biological-sample stimulators include a pneumatic stimulator, a gantry (or other mechanical stimulator), an optical stimulator, a thermal energy tool, and an electrical stimulator, each include different hardware components used to interact with the biological sample 108. The analyzer apparatus 102 can include all the biological-sample stimulators and/or portions that can be removed and/or added. As a particular non-limiting example, in some implementations, a genomic sample is processed and prepared and later sequenced. In such implementations, the optical stimulator may be omitted or otherwise not used.

FIG. 2 illustrates an example of an analyzer apparatus in accordance with various embodiments of the present disclosure. As illustrates and described above, the analyzer apparatus 210 self-configures for processing different sample-processing cartridges using sample-specific configuration circuitry 218. The self-configuration can include a series of state configurations that describe the states of biological-sample stimulators for a specific duration of time and for different biochemical processing.

As illustrated by FIG. 2, the analyzer apparatus 210 can include biological-sample stimulators, such as a pneumatic stimulator 222, a gantry 224, an optical stimulator 212, a thermal stimulator 214, and an electrical stimulator 220. Although the embodiment of FIG. 2 illustrates each biological-sample stimulator as a separate stimulator, components of or all of the respective stimulator can form part of another stimulator. As an example, the thermal stimulator 214, or a component thereof, can be part of the gantry 224. The difference stimulators can be also referred to as subassemblies or subsystems (e.g., a pneumatic subassembly, a mechanical subassembly (e.g., that includes the gantry 224), an optical subassembly, a thermal subassembly, and an electrical subassembly) which are formed of two or more different components, as described herein. Further, each of the stimulators and various components are supported by and integrated with the portable container 216 of the analyzer apparatus 210.

As previously described, the portable container 216 can receive and secure the sample-processing cartridge. The sample-processing cartridge includes a plurality of biochemical processing modules that are self-contained in the board assembly and in fluidic communication with the fluid chambers and channels. The portable container 216 can integrate and support the cartridge assembly 215 that includes at least a cartridge holder that secures the sample-processing cartridges and mechanical couplings that provide connections between the sample-processing cartridge and the biological-sample stimulators of the analyzer apparatus 210. In some embodiments, the analyzer apparatus 210 further includes a cartridge assembly 215. The cartridge assembly 215 includes a cartridge holder, a tray motor and a plurality of mechanical couplings that provide biological-sample stimulators connections and sample-processing cartridge connections used to couple the sample-processing cartridge with the biological-sample stimulators. Although not illustrated, the analyzer apparatus 210 can include a chassis that includes various mounting ports for the biological-sample stimulators, a fan for thermal management, power button(s), and/or status lights or other user interfaces.

The pneumatic stimulator 222, which can also be referred to as a pneumatic subassembly, can control movement of the biological sample through the sample-processing cartridge. For example, the pneumatic stimulator 222 is used to control movement of the biological sample through the sample process-cartridge based on the configuration information. The movement can change constantly through sample processing. The pneumatic stimulator 222 is configured by the configuration processing circuit 221 to deliver volumes, pressures, and flow rates through configurable solenoid valves that enable the processing of the biological sample. The pneumatic stimulator 222 includes at least a pump, tubing, and channels that are used to send forces toward the biological sample and thereby control movement of the biological sample through the sample-processing cartridge. In some instances, the pneumatic stimulator 222 can also be used to mix reagents by creating turbulence in modules for mixing. In various embodiments, the pneumatic stimulator 222 includes one or more pumps, solenoids, tubing and channels, an accumulator, and pressure sensors.

The gantry 224 can selectively provide a plurality of interactions with a biological sample across a plurality of locations of the analyzer apparatus 210. In specific embodiments, the gantry can be referred to or form part of a mechanical subassembly or stimulator. The gantry 224 is coupled to a plurality of interface tools and is used to selectively output different types of energy outputs toward the biological sample to provide different interactions with the biological sample at a plurality of locations across the analyzer apparatus 210. For example, the gantry 224 can enable movement of the interface tools to a plurality of locations, such as any location, within the analyzer apparatus 210. The gantry 224 can be configured by the configuration processing circuit 221 to move various interface tools to the different locations and at the different times for processing the biological sample.

The gantry 224, in specific embodiments and as further illustrated by FIGS. 7A-7E, includes a set of tracks, a bridge framework, and a gantry head, which are coupled to and enclosed by the analyzer apparatus 210. The set of tracks can be parallel to one another and elongate in a first direction, such as along a width or a length of the analyzer apparatus 210. The bridge framework spans the set of tracks and can travel along the tracks in a first direction that the set of tracks elongate in. The gantry head is supported by the bridge framework and travels in a second direction that is perpendicular to the first direction and along the bridge framework. The gantry head includes the plurality of interface tools arranged thereon. For example, the plurality of interface tools can be arranged about or around the periphery of the gantry head. The gantry head can provide a particular physical interaction with the biological sample by rotating the gantry head to align a respective interaction tool with a particular location of the plurality of locations, as further described herein. In specific embodiments, the gantry moves the gantry head to different locations that are between and outside the set of tracks in two-dimensional and/or three-dimensional directions (e.g., X and Y and/or X, Y, and Z) via movement of the bridge framework and/or gantry head. The different interface tools can include a thermal energy tool to heat or cool the biological sample, a magnetic source to apply magnetic forces, an acoustic tool for applying acoustic tools, a motor, and various other interface tools.

As described above, the gantry 224 is used to provide a variety of interactions at different locations within the analyzer apparatus 210, which can allow for flexibility for physical interactions (e.g., heat, acoustics, magnetic) with the biological sample. The configuration processing circuit 221 can instruct the gantry 224 to provide the different interactions at the different locations and at corresponding times during processing of the biological sample. The gantry head can be pre-installed with a fixed set of capabilities, the interface tools can be detachable and different tools can be attached and/or the gantry head can be detachable from the bridge framework to provide additional field configurable capabilities. For example, the gantry head can detach from the bridge framework and the bridge framework can be attached to another gantry head having a different set of interface tools than the gantry head. In various embodiments, the gantry 224 has a default position which is used to align the gantry 224 and/or the gantry head to the sample-specific cartridge. The default position can include a predefined location (e.g., a home or zero position) in the portable container that the gantry 224 moves to or is located in when the analyzer apparatus 210 is not processing a cartridge, when a cartridge is first inserted into the analyzer apparatus, and/or in the event of an error, such as the gantry not aligning with cartridge. In specific embodiments, the default position can include specific X, Y, and Z coordinate locations.

The thermal stimulator 214, which can also be referred to as a thermal subassembly, can provide temperature control at specific locations and time. The thermal stimulator 214, in specific embodiments, is a thermal energy tool that includes a heat source and/or a cooling source, such as a TEC, and, optionally, a thermistor used to provide the temperature control. The thermal energy tool uses the heat source and/or cooling source to output thermal energy toward the biological sample or otherwise provides a transfer of thermal energy from the biological sample, and thereby provides temperature control at specific locations and time. The thermal stimulator 214, or a portion thereof (e.g., the TEC), can be part of the gantry 224, such as an interface tool of the gantry apparatus. The thermal stimulator 214 provides temperature control at specific locations and times to enable the customized sample processing required by the sample-processing cartridge. The thermal stimulator 214 and/or the thermal energy tool can include a TEC, thermistor, heat sinks, and/or a translation mechanism. In certain instances, the thermal stimulator 214 can be held in a defined location, but in most cases at least a portion of the thermal stimulator 214 (via the TEC) is movable by the gantry 224. The configuration processing circuit 221 provides instructions to the thermal stimulator 214 (e.g., the thermal energy tool) on the temperature and duration required of the thermal stimulator 214 to accomplish the biological sample processing, while the gantry 224 can be used to locate the specific thermal component at the defined spatial location.

The electrical stimulator 220, which can also be referred to as an electrical subassembly, can control timing of the other biological-sample stimulators. In specific embodiments, the electrical stimulator 220 can be used to process image data for providing diagnostic results. The electrical stimulator 220 includes circuitry configured and arranged to output timing signals for controlling actions performed by other of the plurality of biological-sample stimulators. The electrical stimulator 220 can also provide the necessary voltage and current requirements for the gantry 224, optical stimulator 212, pneumatic stimulator 222, and thermal stimulator 214 to provide the required forces, laser power, pressure or flow rates, and temperatures as relayed by the sample-processing cartridge through the configuration processing circuit 221. The electrical stimulator 220 can include a power source, input/output interfaces, processing circuitry (e.g., a central processor), a Peripheral Interface Controller (PIC), an analog to digital converter, a data port, among other electrical components.

The optical stimulator 212 can capture image data of the biological sample. The optical stimulator 212, which can also be referred to as an optical subassembly, includes at least a light source and detector circuitry used to output an optical signal toward the biological sample and capture image data of the biological sample responsive to the optical signal. For example, the sample-processing cartridge can include an assay used for capturing targets, such as specific nucleic acids, antibodies, and/or other targets. The optical stimulator 212 can capture image data of the targets, which may include fluorescent tags, as further described herein. As a specific example, the optical stimulator 212 can be used for DNA sequence specific target analysis. The optical stimulator 212 can include an imaging camera, excitation laser, and optical relay with the biological sample moved to the optical stimulator 212 by the pneumatic stimulator 222 and stringency provided by the thermal stimulator 214. The configuration processing circuit 221 provides instructions for the optical stimulator 212 to set the exposure times, exposure laser power and duration, stringency temperatures, and spatial location for each sequence specific feature on the sample-processing cartridge. In various embodiments, as further described below, the optical stimulator 212 can include a light source (e.g., laser), illumination optics, collection optics, detector circuitry, and data transport, among other components.

As a specific example, the optical stimulator 212 includes a light source that emits a light beam (e.g., a polarizing light beam), and detector circuitry. The optical stimulator 212 is configured to selectively optically interrogate a substrate that is part of the sample-processing cartridge, such as an array (e.g., provide the beam of light to particular locations of the array). For example, the optical stimulator 212 has a surface adapted to allow placing thereon a substrate (e.g., a microarray). In other embodiments, the optical stimulator 212 includes a digital micromirror device (DMP). Further, in specific embodiments, the optical stimulator 212 includes a mechanical mechanism, such as a wheel that the digital microarray is placed on that rotate and/or that rotates the location of the light beam on the digital light beam. Such a mechanical mechanism can be an interface tool located on the gantry head of the gantry, in specific embodiments.

The light beam is selectively directed to particular locations of the substrate (e.g., array). For example, the light beam from the light source is reflected by the surface to provide an evanescent field over a location of the substrate such that the location of a substrate in the evanescent field causes a polarization change in the light beam. The optical stimulator 212 can include a confocal laser as the light beam.

The detector circuitry detects an optical signal in response to the light beam being selectively directed to locations of the substrate (e.g., a digital microarray). In specific embodiments, the detector circuitry is positioned to detect the polarization change in the light beam as the light beam is scanned over the substrate (e.g., a microarray). The polarization change in the light beam and/or the detected signal is indicative of the fluorescent signal at the particular location of the substrate. Processing circuitry is coupled to the detection circuitry to process an optical signal from the detection circuitry to obtain a representation of the fluorescent signal at the location of the substrate (e.g., the intensity of the fluorescent signal). Further, the processing circuitry processes a plurality of optical signals to obtain representations of florescent signals at a plurality of locations of the substrate. The detector circuitry can include various lenses and/or optical wavelength guides. The optical stimulator 212, in some instances, is and/or includes imaging circuitry, such as a charged coupled device (CCD).

In various embodiments, the processing circuitry is configured to perform repetitive comparative measurements of the optical signals from plurality of locations of the substrate (e.g., an array). The processing circuitry uses the captured optical signals to provide the output indicative of an analysis performed. Example scanner systems include the Tecan™ Power Scanner or the GenePix™ 4000B Microarray Scanner (e.g., a microarray scanner) and the processing circuitry can utilize various computer-readable medium to analyze the results of the microarray, such as the Array-Pro™

Analyzer or the GenePix™ Pro Microarray Analysis Software (e.g., Acuity™). The processing circuitry of the optical stimulator 212, in some specific embodiments, can include a central processor that forms part of the sample-specific configuration circuitry 218, the electrical stimulator 220, and/or the optical stimulator 212.

In specific embodiments, the substrate has a plurality of complementary tag sequences at a plurality of different locations on a substrate (e.g., a microarray), which can be referred to as complementary tag locations. The complementary tag sequences are configured to bind to different probes. The sample is exposed to the plurality of probes. For example, a plurality of sets of different probes can be placed in contact with a biological sample from an organism. Example biological samples include blood, tissue, saliva, urine, etc., taken from an organism, such as a human.

The detector circuitry scans the substrate, and therefrom, captures the signals (e.g., optical intensities) indicative of a tag sequence bound to the substrate. The detector circuitry can provide the captured signals to the processing circuitry. The processing circuitry uses the captured signals, in addition to information indicative of the different locations and associated tag sequences, to assess a number of each of the target sequences present in the sample. For more specific and general information of example arrays and analysis performed thereon including a digital output technique, reference is made to PCT Application (Ser. No. PCT/US2017/024098), entitled "Apparatuses and Methods for Assessing Target Sequence Numbers," filed Mar. 24, 2017 (for example, as illustrated by FIGS. 6 and 7A-7E of the patent document). For more specific and general information on example sample-processing cartridges, including a modular cartridge that can be configured for different uses, reference is made to U.S. application Ser. No. 15/304,030 entitled "Portable Nucleic Acid Analysis System and High-Performance Microfluidic Electroactive Polymer Actuators," filed Oct. 13, 2016, each of which are fully incorporated herein by reference for their teachings (e.g., for example, as illustrated by FIGS. 2A-2C of the patent document). Although embodiments are not limited to assessing target sequence numbers, and can include a variety of different arrays and assessments.

The various stimulators and/or hardware components illustrated by FIG. 2 can interface with one another and/or form part of one another. For example, the optical stimulator 212 can interface with the electrical stimulator 220 by the electrical stimulator 220 providing laser power, camera power, and camera communications. The optical stimulator 212 can also interface with the cartridge assembly 215 by translating to the substrate for imaging. The electrical stimulator 220 can additionally interface with the thermal stimulator 214 by providing TEC power and thermistor values, with the pneumatic stimulator 222 by providing solenoid power, pump power, and pressure sensing, and/or with the chassis by providing communication input (e.g., Ethernet input for downloading data) and power input.

The data located on the sample-processing cartridge is used to provide the configuration information to the analyzer apparatus 210 via the sample-specific configuration circuitry 218. The sample-specific configuration circuitry 218 provides the location and requirements of specific biological processing modules on the sampled-processing cartridge. The location information can provide the x, y and/or z coordinate locations of interface features for the gantry 224, thermal stimulator 214, pneumatic stimulator 222, and/or optical stimulator 212 to interface with the sample-processing cartridge.

As illustrated, the sample-specific configuration circuitry 218 includes a memory circuit 223, an identification circuit 219 and a configuration processing circuit 221. The memory circuit 223 stores and is used to access configuration information specific to respective sample-processing cartridges. The identification circuit 219 can identify the sample-processing cartridge using the data located on the sample-processing cartridge and identify the configuration information using the data. The data can include a barcode, such as matrix barcode (e.g., a quick response (QR) code) located on the sample-processing cartridge scanned by the identification circuit 219, data stored in a radio frequency tag on the sample-processing cartridge and read by the identification circuit 219, and/or a memory or cloud-based location provided by the sample-processing cartridge (such as via a bar code or QR code that identifies the memory or cloud-based location). The identification circuit 219 can include components used to scan the code, read the data, and/or the communication circuit to download the configuration information from the memory or cloud-based location.

The memory location can include a location on a memory circuit of the analyzer apparatus 210 (e.g., the memory circuit 223 of the sample-specific configuration circuitry 218), a memory location on an external processing circuitry (e.g., external controller in communication with the analyzer apparatus 210), and/or a cloud-based location. In various specific embodiments, the configuration information is included in the data on the sample-processing cartridge. In some embodiments, the analyzer apparatus 210 is in communication with an external processing circuitry, such as an external controller. The external processing circuitry can include a user interface, a bar code or radio frequency identification (RFID) reader, and can be in communication with the analyzer apparatus 210. For example, the external processing circuitry can provide patient information to the analyzer apparatus 210, receive final data from the analyzer apparatus 210 and/or use the data to generate a report. The external processing circuitry and analyzer apparatus 210 can communicate wirelessly or in a wired manner (e.g., Ethernet). In other embodiments and/or in addition, the analyzer apparatus 210 includes an RFID reader and/or barcode reader. The analyzer apparatus 210 can communicate the data to the external processing circuitry to identify the configuration information and/or can otherwise use the data to identify the configuration information. For example, the analyzer apparatus 210 can use the data to obtain the configuration information, which may be included in the data, or from a memory location external or internal to the analyzer apparatus 210. The analyzer apparatus 210 can further be configured to collect image data, analyze the image data, and output an analysis using an internal processing circuitry.

The configuration information can be accessed and stored prior to performing the process on the biological sample, as previously described (although embodiments are not so limited). In some specific embodiments, once an analyzer apparatus accesses and stores, e.g., downloads, the configuration information for a first type of test, the configuration information is stored on the memory circuit internal to the analyzer apparatus 210 and subsequently used for another sample-processing cartridge to perform the first type of test on a different sample. As a specific example, a first sample-processing cartridge is inserted into the analyzer apparatus. The analyzer apparatus identifies that the first sample-processing cartridge is associated with testing a blood sample of a human for DNA targets associated with ten different types of cancer. The sample-processing cartridge includes data for identifying the type of test and/or accessing the configuration information associated with the test (e.g., internal or external). Subsequent to processing the first sample-processing cartridge, a second sample-processing cartridge is inserted into the analyzer apparatus. The analyzer apparatus identifies that the second sample-processing cartridge is associated with testing a blood sample of another human for DNA targets associated with the same ten different types of cancer (e.g., is associated with the same test as the first sample-processing cartridge). The analyzer apparatus accesses the internal memory location used to store the configuration information for the first sample-processing cartridge and, optionally, without accessing or downloading the configuration information from an external location. In this manner, the analyzer apparatus can be configured for different tests based on sample-processing cartridges inserted therein, and can store the configuration information for subsequent tests. Although embodiments are not so limited, and can include downloading the configuration information for each cartridge.

The configuration information, which can also be referred to as a "configuration file," can include a series of state configurations that describes the state of all biological-sample stimulators (e.g., hardware components) for a specific duration of time. The configuration information can provide the analyzer apparatus 210 with the spatial location of specific biochemical processing modules of sample-processing cartridge along with identification of the selected biological-sample stimulators of the plurality used for performing the analysis and time requirements (e.g., the different times associated with the spatial location and interactions). The configuration processing circuit 221 can process the configuration information and provide the series of state configurations. For example, the configuration processing circuit 221 can provide the location and requirements of specific biological processing modules on the sample-processing cartridge. The location information provides the x, y and z coordinate locations of interface features for the gantry 224, thermal stimulator 214 (e.g., thermal energy tool), pneumatic stimulator 222, electrical stimulator 220, and optical stimulator 212 to interface with the sample-processing cartridge and thereby cause the interaction with the biological sample.

In accordance with various embodiments, the sample-specific configuration circuitry 218 can configure the analyzer apparatus 210 for the series of state configurations by providing spatial location information of specific biochemical processing modules self-contained in the sample-processing cartridge along with timing information and identification of the selected biological-sample stimulators of the plurality used for performing the analysis at the different times. The sample-specific configuration circuitry 218, such as via the configuration processing circuit 221, can instruct the selected biological-sample stimulators to interface with specific biochemical processing modules of the sample-processing cartridge based on parameters identified by the configuration information. The parameters can include spatial locations of the biochemical processing modules, the selected biological-sample stimulators used to interface with the biochemical processing modules, corresponding times for the interfacing, and interface parameters indicative of the interactions with the biological sample. As specific examples, the parameters include specific instructions for the selected biological-sample stimulators interfacing with the biochemical processing modules including time requirements of the interface and/or interaction, two-dimensional or three-dimensional locations within the sample-processing cartridge for the interface, and values of the interface (e.g., temperature, magnetic and mixing).

The sample-specific configuration circuitry 218 can thereby configure the biological-sample stimulators for the series of state configurations that are specific to the sample-processing cartridge and based on data identified directly from or otherwise associated with the sample-processing cartridge. The series of state configurations include locations and requirements of specific biological processing modules on the sample-processing cartridge and parameters for respective biological-sample stimulators.

In further embodiments, the analyzer apparatus 210 can include one or more sensors. The sensors can be used to provide feedback on the status of the parameters, such as verifying that the correct interaction is occurring at the correct location and with the correct interface values. In some embodiments, the feedback provided by the sensors may indicate that the gantry is not properly aligned with the sample-processing cartridge. In such embodiments, the gantry is instructed to return to the default position to re-align with the sample-processing cartridge. Although embodiments are not so limited and in some specific embodiments the sensors are used to adjust the alignment of the gantry without returning to the default position.

Although the above describes the analyzer apparatus 210 self-configuring by identifying data on the sample-processing cartridge, embodiments are not so limited. For example, the analyzer apparatus 210 can self-configure by a user entering a code into the analyzer apparatus 210 and the code identifying the series of state configurations. In other example embodiments, a configuration file is uploaded to the analyzer apparatus 210, such as from external processing circuitry.

Further, in various embodiments, the sample-processing cartridge can include a means for a user to configure the sample-processing cartridge. For example, the user can mark a step by hand on the sample-processing cartridge, such as a label which is read by the analyzer apparatus and/or manually entered into the sample-processing cartridge by another user. In other embodiments, the specific-instructions are coded into the data on the sample-processing cartridge that is read by the analyzer apparatus.

Figure 3:
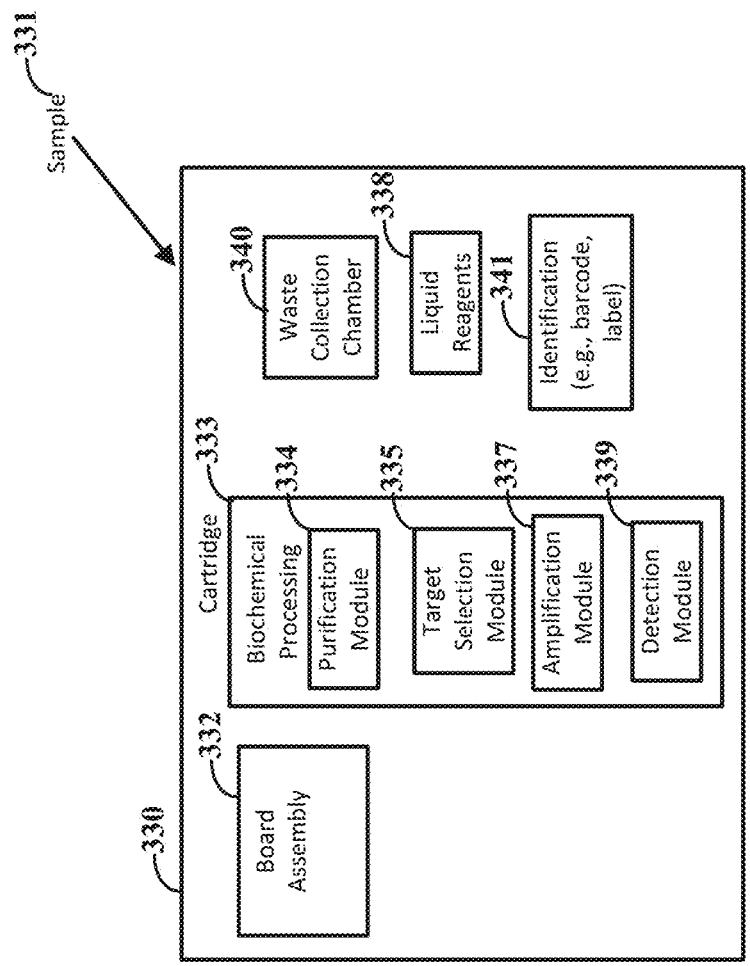
FIG. 3 illustrates an example of a sample-processing cartridge in accordance with various embodiments of the present disclosure.

FIG. 3 illustrates an example of a sample-processing cartridge in accordance with various embodiments of the present disclosure. The sample-processing cartridge 330 can include a board assembly 332, a plurality of biochemical processing modules 333, an input port for receiving a biological sample 331, and (identification) data 341. The board assembly 332 has fluid chambers and channels for processing a biological sample therein. The plurality of biochemical processing modules 333 are self-contained and/or otherwise coupled to the board assembly 332 and in fluidic communication with the fluid chambers and chambers.

The data 341 located on the sample-processing cartridge 330 provides configuration information specific to the sample-processing cartridge for configuring an analyzer apparatus to perform the biochemical processing using the plurality of biochemical processing modules 333. The data 341, as described above, can include a barcode, a radio frequency tag, and/or identification of a cloud-based location or other memory location, such as a link indicative of the cloud-based location or other memory location.

The biochemical processing modules 333 are configured to perform biochemical processing on the biological sample 331. Example modules, as illustrated, include a purification module 334, a target selection module 335, an amplification module 337, and a detection module 339. Embodiments are not limited to the specific modules illustrated by FIG. 3 and can include a variety of modules for different analysis, as further described in connection with FIGS. 8A-8E. The modules can additionally include a sample collection module used to interface with a biological sample container and/or transfer device, such as a blood tube, and includes a sample chamber configured to hold a volume of the biological sample.

In specific embodiments, the purification module 334 can perform extraction of targets within the biological sample. For example, the purification module can mix the sample with enzymes and chemicals to release the targets from the biological sample. The targets can include DNA, RNA, and antibodies, among other types of targets. In specific embodiments, the purification module 334 can include a proteinase K (PK) chamber that contains PK, and a TEC interface to allow for engagement with the TEC. The PK chamber can include other chemicals, such as a detergent and/or salts. The PK chamber is heated, via the TEC, to activate PK and is mixed with the biological sample to release the targets (e.g., bound DNA) bound to other components in the biological sample (via the pneumatic stimulator). The purification module 334 can further perform target isolation, in some embodiments. For example, the purification module 334 can include binding chamber(s), one or more binding elements, and the TEC interface. The binding elements can include beads or a solid support, such as a silica frit, as further described herein. In some embodiments, the purification module 334 include two separate modules, e.g., an extraction module and an isolation module, that perform the functions described above.

The target selection module 335 can be used to bind specific targets to probes. The target selection module 335 can include one or more chambers, probes and enzymes, and a TEC interface. For example, probes can be mixed with the isolated targets from the purification module 334 and the targets are annealed to the probes.

The amplification module 337 can be used to amplify the targets bound to the probes via a PCR process, as further described herein. The amplification module 337 can include probes, universal PCR primers, enzymes and other reagents, and a TEC interface. In some embodiments, the target selection module 335 and the amplification module 337 include one module, e.g., a library preparation module that perform the functions described above.

The detection module 339 can be used to bind the amplicons to a substrate and detect the bound amplicons, which include targets bound to probes, as further described herein. The detection module 339 can include a mixing chamber used to prepare a hybridized sample, a hybridization chamber, a microarray or other substrate, and interfaces to various hardware components (e.g., TEC, laser, optics). In various embodiments, the detection does not occur on the analyzer apparatus, and the sample-processing cartridge 330 does not include the detection module 339.

The sample-processing cartridge 330 can include various additional components. For example, the sample-processing cartridge 330 can include a liquid reagents module 338 that contains various reagents used for processing the biological sample 331. The liquid reagents module 338 may be pierced by the analyzer apparatus responsive to placement of the sample-processing cartridge 330 in a cartridge assembly, and which results in liquid communications between the liquid reagents module 338 and one or more other modules and/or chambers of the board assembly 332. The sample-processing cartridge 330 can additionally include a waste collection chamber 340 used to collect various fluids and material after various processes.

Figure 4:
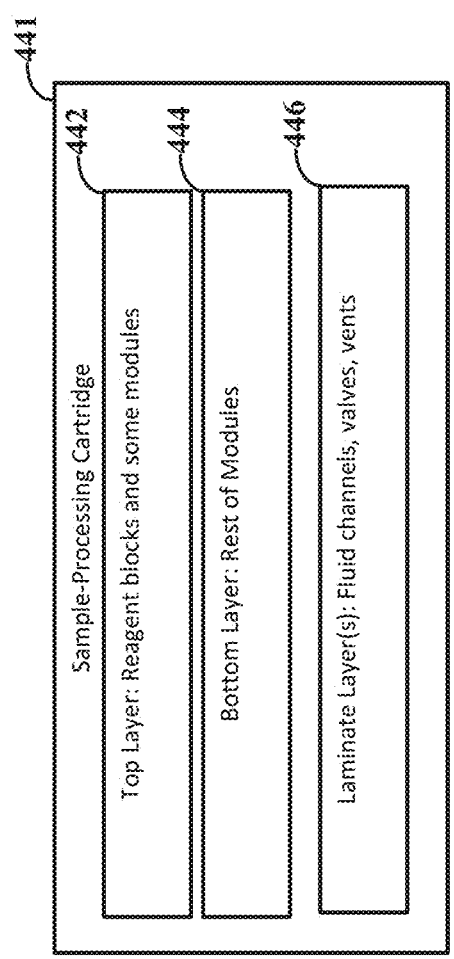
FIG. 4 illustrates examples of layers of a sample-processing cartridge in accordance with various embodiments of the present disclosure.

FIG. 4 illustrates examples layers of a sample-processing cartridge in accordance with various embodiments of the present disclosure. As illustrated, the sample processing cartridge 441 can be formed in a variety of layers. The top layer 442 can include the reagents module and other modules, such as various modules that are moved to by the gantry (or other mechanical subassembly) of the analyzer apparatus. The bottom layer 444 can include remaining modules, such as the substrate (e.g., an array). And, below the bottom layer 444 can include a laminate layer 446 that includes the fluid channels, valves, and vents.

Figure 5:
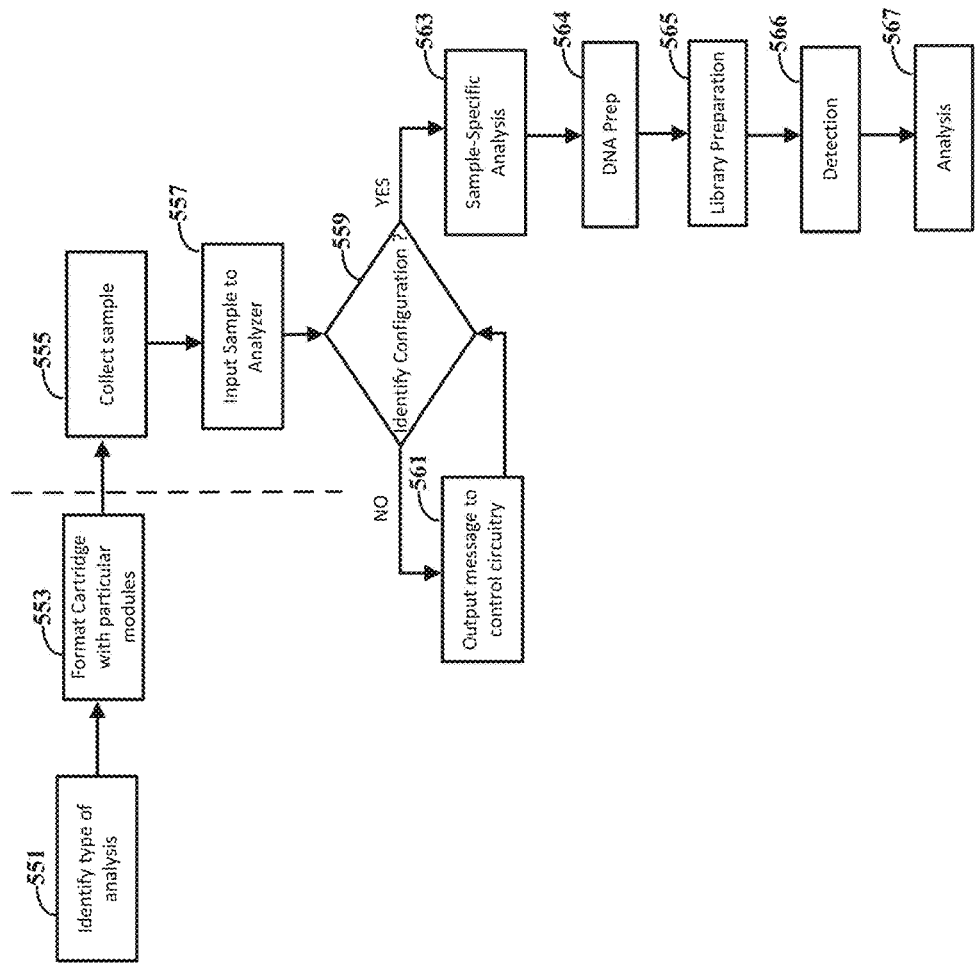
FIG. 5 illustrates an example method of self-configuring an analyzer apparatus in accordance with various embodiments of the present disclosure.

FIG. 5 illustrates an example method of self-configuring an analyzer apparatus in accordance with various embodiments of the present disclosure. As described above, prior to processing a biological sample, configuration information is identified and/or loaded into the analyzer apparatus, such as via software or obtained using data on the sample-processing cartridge, and that prescribes the state configurations for each step of the sample processing. The biological sample can be processed in a number of different ways depending on the type of analysis and/or diagnostic assay being run. Sample preparation is accomplished using a variety of different biochemical processes. A specific example of biochemical processes that can be run on the analyzer apparatus are described below and include DNA extraction, DNA isolation, biotinylation, probe annealing, probe extension, universal amplification, and microarray hybridization in some specific embodiments used for detecting DNA targets.

Figure 10:
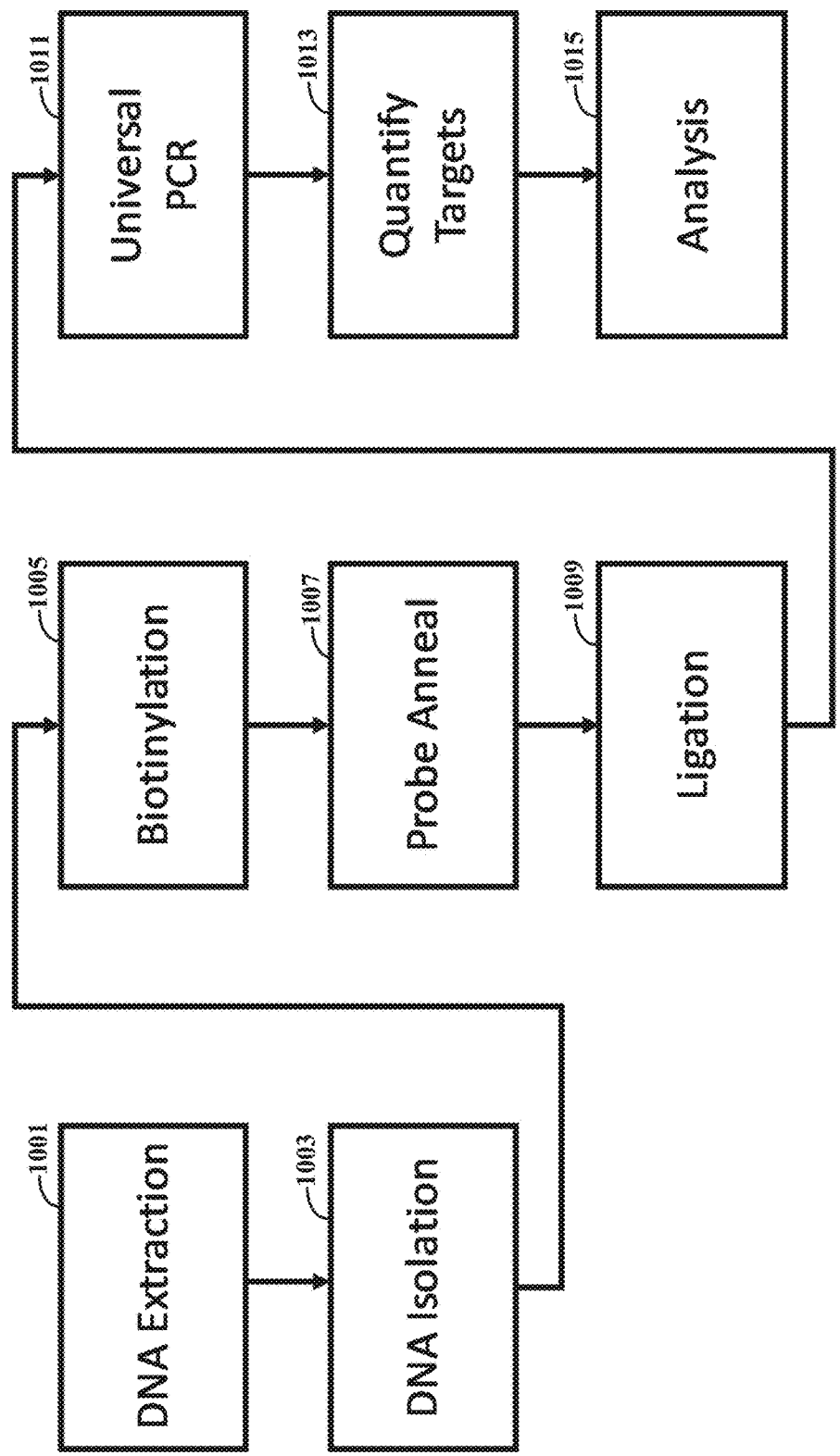
FIG. 10 illustrates an example method of using an analyzer apparatus for performing an analysis on a sample, in accordance with various embodiments of the present disclosure.
Figure 11:
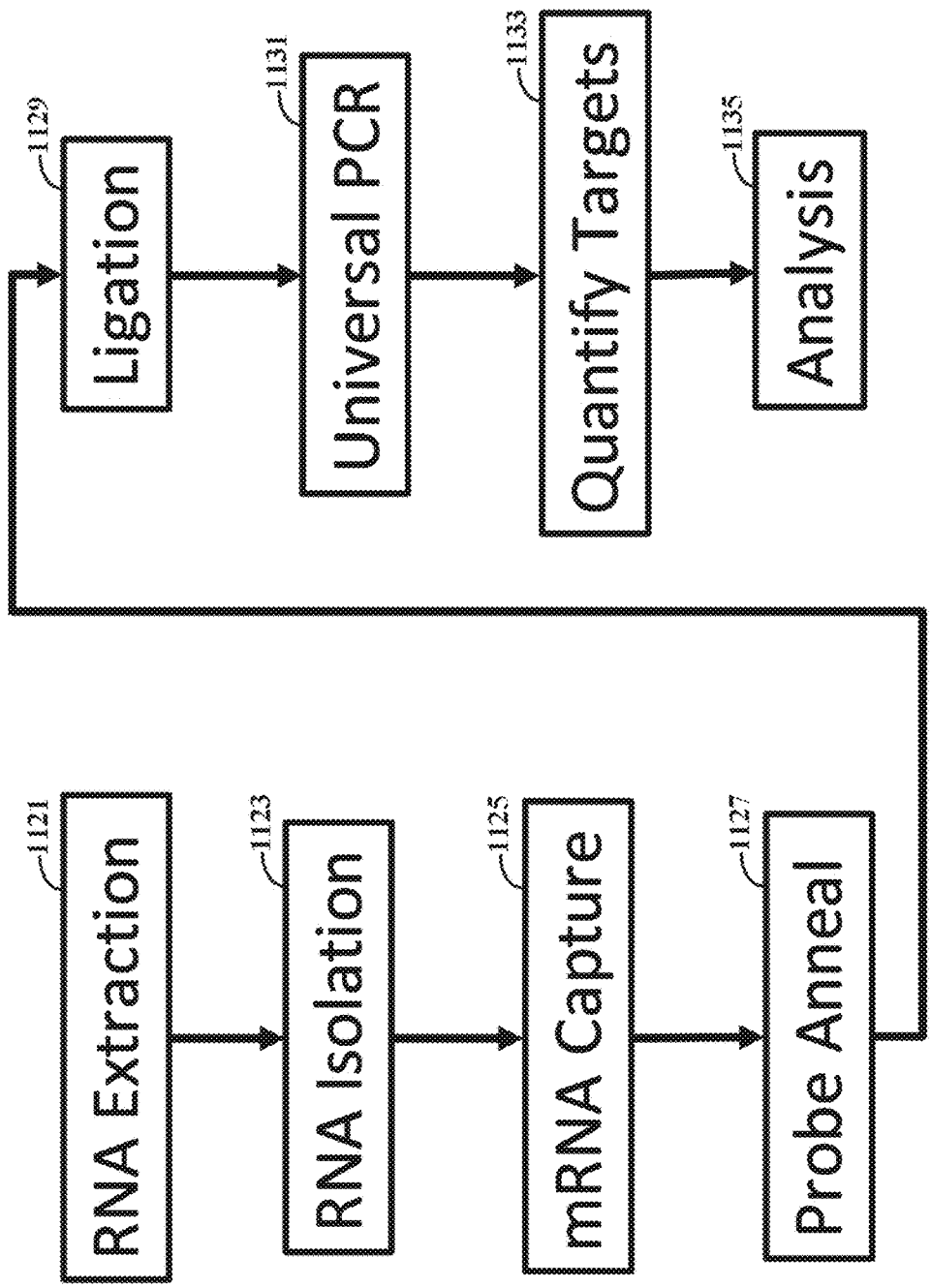
FIG. 11 illustrates an example method of using an analyzer apparatus for performing an analysis on a sample, in accordance with various embodiments of the present disclosure.

Example approaches use solid supports (streptavidin biotin binding or DNA binding to silica frits), ligases, terminal transferases, DNA polymerases, RNA reverse transcriptases, uracil DNA glycosylate, exonucleases, DNA probe annealing to templates, and other enzymes. Each of these biochemical processes can use different reaction volumes, temperatures, times, and (physical) interactions with the biological sample. The requirements are not uniform and therefore static locations of biological-sample stimulators and/or hardware components thereof (e.g. TECs, magnets, and mixers) does not allow for performing multiple different workflows. Example configurations of modules for specific diagnostic testing are shown in FIGS. 10 and 11. These are given as examples, but other common biological sample processing workflows can be implemented on the field configurable analyzer apparatus.

The method as illustrated by FIG. 5 can include providing a sample-processing cartridge comprising a board assembly with fluid chambers, channels and a biological sample therein. Optionally, in some embodiments (as illustrated by the dashed line), the method can include formatting a sample-processing cartridge for a specific analysis. For example, the type of analysis can be identified, at 551, and a sample-processing cartridge can be formatted with particular biochemical processing modules to perform the respective biochemical processes and in the respective order, at 553. Additionally, in some embodiments, data is located on the sample-processing cartridge such that the analyzer apparatus identifies configuration information specific to the sample-processing cartridge without or with minimal user input. In other embodiments, the sample-processing cartridge can be preconfigured for a specific analysis. A sample from a patient (e.g., human or other organism) can be collected, at 555, and input to an input port of the sample-processing cartridge.

The sample-processing cartridge can be provided to an analyzer apparatus, such as by placing the sample-processing cartridge into a cartridge assembly of the analyzer apparatus, at 557. In response thereto, sample-specific configuration circuitry of the analyzer apparatus can identify configuration information specific to the sample-processing cartridge by scanning a location of the sample-processing cartridge for data. The analyzer apparatus can verify that the configuration information is identified, at 559. If the configuration information is not identified, the analyzer apparatus can output a message, such as a message on a user interface of the analyzer apparatus, a message to other circuitry (e.g., external processing circuitry accessibly by a technician), and/or other indications on the analyzer apparatus (e.g., buzzing sound or flashing light indicating an error), at 561.

In response to verification of identified configuration information, the analyzer apparatus is configured for a series of state configurations to perform the analysis on the biological sample, at 563. As previously described, configuring the analyzer apparatus for the series of state configurations can include providing spatial location information of specific biochemical processing modules self-contained in the sample-processing cartridge along with timing information and identification of the selected biological-sample stimulators of the plurality used for performing the analysis and at the different times. In specific embodiments, the configuration can include directing ones of the selected biological stimulators to interface with the respective biochemical processing modules of the sample-processing cartridge at different times during the analysis based on the spatial locations of the biochemical processing modules, and interface parameters indicative or associated with interaction(s) with the biological sample.

FIG. 5 further illustrates an example of a plurality of biochemical processes that the analyzer apparatus is configured for. As illustrated, the biochemical processes can include DNA preparation at 564, library preparation at 565, and detection/analysis at 566 and 567. In a specific embodiment, DNA preparation can include DNA extraction and isolation, library preparation can include annealing, ligation, and/or PCR, as further described herein.

FIG. 6 illustrates another example method of self-configuring an analyzer apparatus in accordance with various embodiments of the present disclosure. In various embodiments, the analyzer apparatus may be configured at manufacturing for particular uses. In such embodiments, a different analyzer apparatus is used for different analysis. As illustrated by the dashed line, the method can optionally include formatting a sample-processing cartridge for a specific analysis. For example, the type of analysis can be identified, at 670, and a sample-processing cartridge can be formatted with particular biochemical processing modules to perform the respective biochemical processes and in the respective order, at 671. The analyzer apparatus can be configured at manufacturer for the specific analysis, at 672. The analysis can include a series of state configurations for selected biological-sample stimulators of the analyzer apparatus and at different times, as previously described.

A biological sample from a patient (e.g., human or other organism) can be collected and input to an input port of the sample-processing cartridge, at 673. The sample-processing cartridge can be provided to an analyzer apparatus at 674, such as by placing the sample-processing cartridge into a cartridge holder. In response, the analyzer apparatus, using the pre-configured series of state configurations, perform the analysis on the biological sample. As previously described, configuring the analyzer apparatus for the series of state configurations can further includes providing spatial location information of specific biochemical processing modules self-contained in the sample-processing cartridge along with timing information and identification of the selected biological-sample stimulators of the plurality used for performing the analysis and at the different times.

Similarly to FIG. 5, FIG. 6 further illustrates an example of a plurality of biochemical processes that the analyzer apparatus is configured for. As illustrated, the biochemical processes can include DNA preparation at 675, library preparation at 676, and detection/analysis at 677 and 678. In a specific embodiment, DNA preparation can include DNA extraction and isolation, library preparation can include annealing, ligation, PCR, as further described herein.

FIGS. 7A-7F illustrate example gantry apparatuses and/or analyzer apparatuses including a gantry in accordance with various embodiments of the present disclosure. As previously described, various embodiments are directed to a gantry apparatus such as a gantry and/or an analyzer apparatus that includes a gantry. The gantry can be used to selectively provide a plurality of interactions with a biological sample, as contained in a sample processing cartridge, across a plurality of locations of an analyzer apparatus. For example, the gantry includes a plurality of interface tools that selectively output different types of energy toward the biological sample to provide different interactions with the biological sample. The gantry can enable movement of the interface tools to any location within the analyzer apparatus by moving the interface tools in an X, Y, and/or Z direction.

Figure 7A:
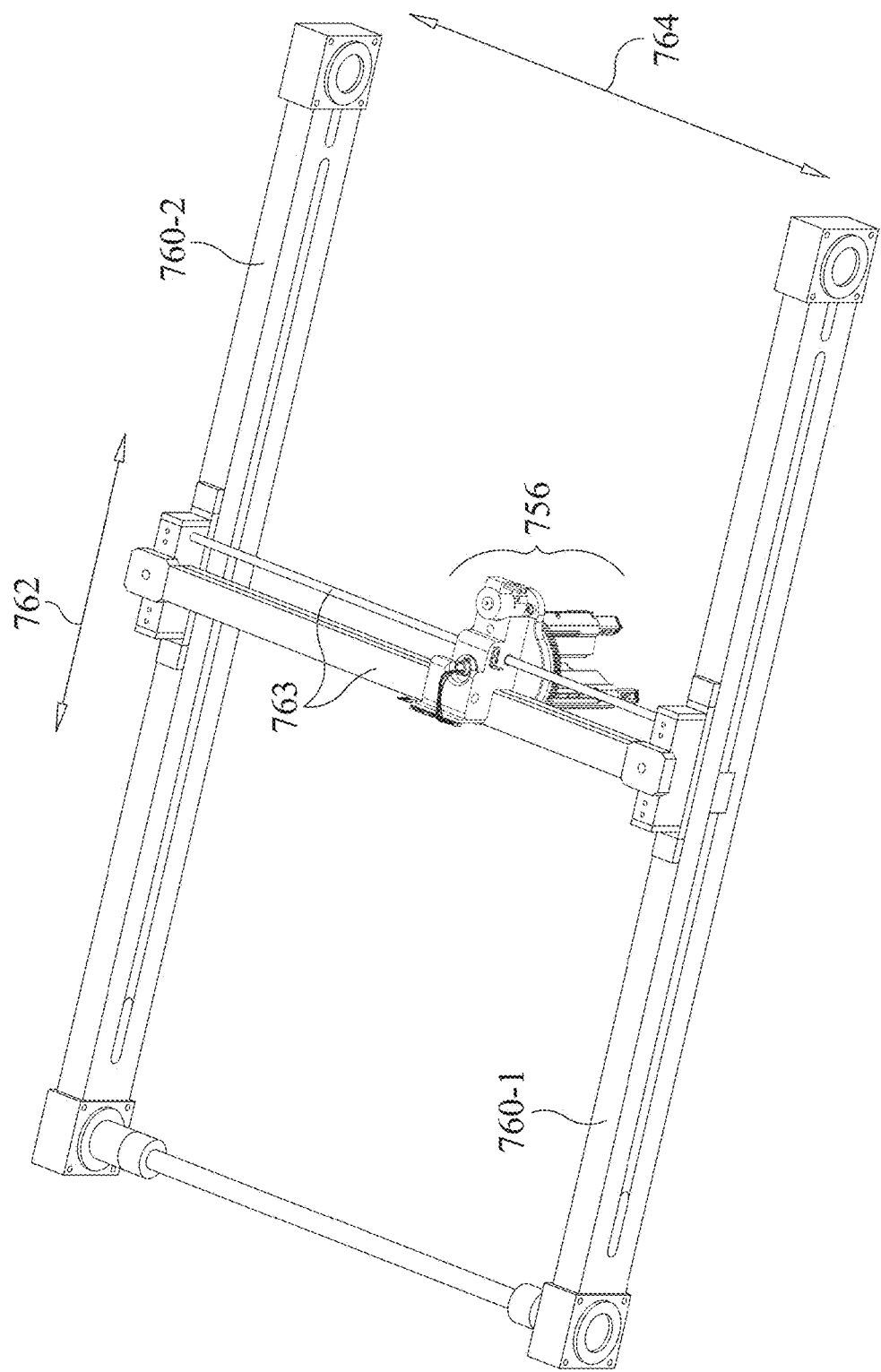

FIG. 7A illustrates an example of a gantry apparatus in accordance with various embodiments. As illustrated, the gantry apparatus includes a set of tracks 760-1, 760-2, a bridge framework 763, and a gantry head 756. The set of tracks 760-1, 760-2 are arranged parallel to one another and the bridge framework 763 spans the set of tracks. For example, the bridge framework can be perpendicular to the set of tracks, although embodiments are not so limited and the bridge framework can be at a variety of angles to the set of tracks. The gantry, in specific embodiments and as further illustrated herein, is enclosed by the analyzer apparatus. The set of tracks 760-1, 760-2 can be parallel to one another and elongate in a first direction 762, such as along a width or a length of the analyzer apparatus. The bridge framework spans the set of tracks in a second direction 764 and can travel along the set of tracks in a first direction 762 that the set of tracks elongate in. The gantry head 756 is supported by the bridge framework and travels in a second direction 764 that is perpendicular (or at another angle) to the first direction and along the bridge framework. The gantry head 756 includes the plurality of interface tools arranged thereon. The gantry head 756 can provide a particular physical interaction with the biological sample by rotating the gantry head to align a respective interface tool with a particular location, as further described herein. In specific embodiments, the gantry moves the gantry head 756 to different locations that are between and outside the set of tracks in two-dimensional and/or three-dimensional directions (e.g., X and Y and/or X, Y, and Z) via movement of the bridge framework and/or gantry head. The different interface tools can include a thermal energy tool to heat or cool the biological sample (e.g., a TEC), a magnetic source to apply magnetic forces, an acoustic tool for applying acoustic tools, a motor, and various other tools.

In accordance with various embodiments, the gantry apparatus can move the gantry head to different locations using a variety of mechanisms, such as one or more rotors coupled to components of the gantry apparatus. Other mechanisms, as would be appreciated by one of ordinary skill in the art, can include rotating wheels or other types of rotating components, gears and/or rotary gear systems, pulleys, crank and shafts and/or crankshafts and rods, collars, couplings, cams, clutches, flywheels, shaft ends, spindles, meshing gears, and horizontal or vertical shafting, among other types of mechanisms.

Figure 7B:
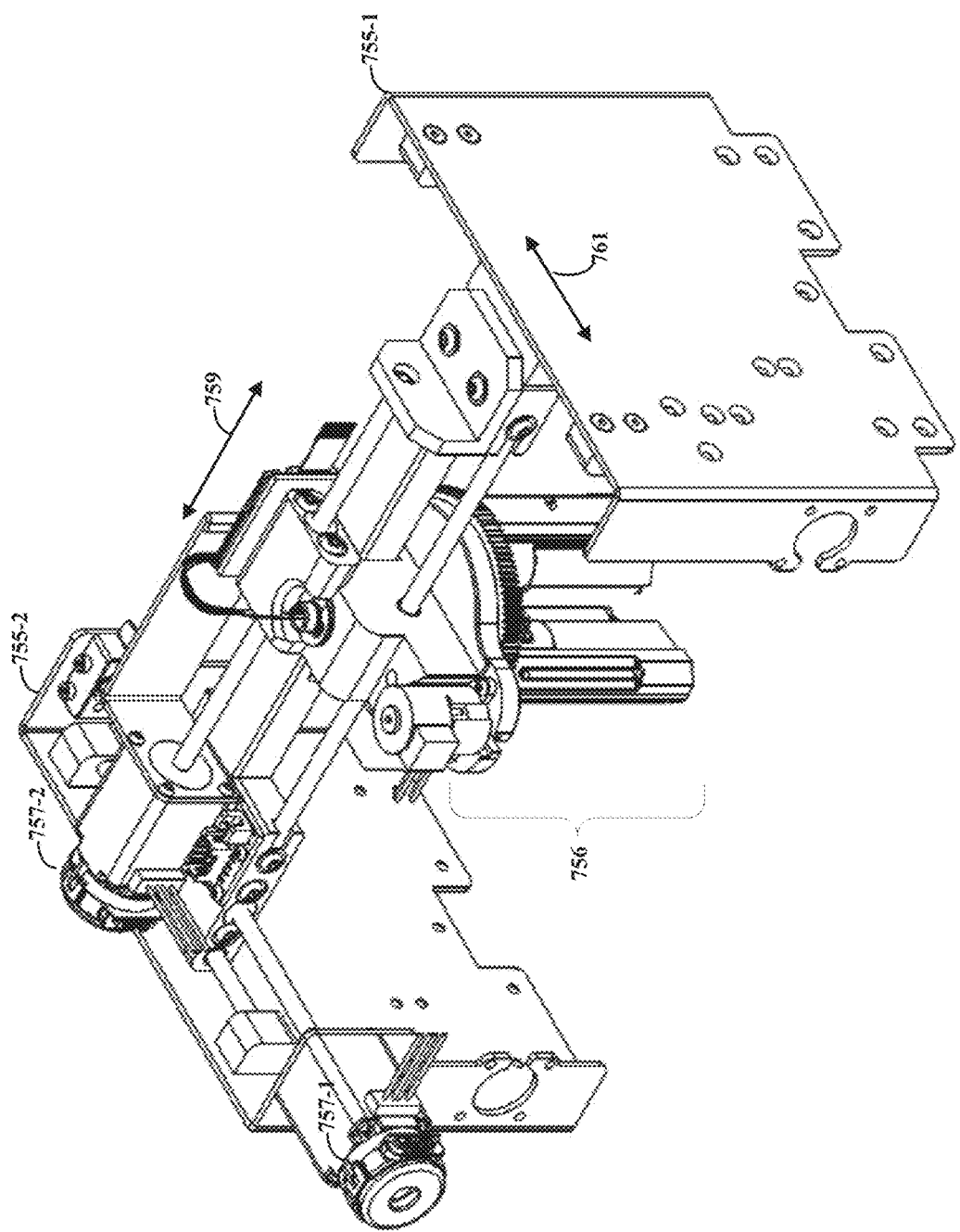

FIG. 7B illustrates a more specific example of a gantry apparatus in accordance with various embodiments. The gantry apparatus includes brackets 755-1, 755-2 that support the set of tracks and that can be mounted or otherwise coupled to the frame of the portable container of the analyzer apparatus. Each of the tracks of the set or at least one of the tracks are formed by or include at least one arm (or a set of arms) that is coupled to a rotor 757-1. Rotation of the rotor 757-1 (and optionally another rotor coupled to the other arm) moves the arm(s) coupled thereto, as well as the bridge framework spanning the set of tracks, in a first direction 761, such as along a width or a length of the analyzer apparatus. The bridge framework spans the set of tracks and is configured to travel along the set of tracks in the first direction 761 responsive to movement of the rotor 757-1 and the arm coupled to the rotor 757-1. A gantry head 756 is supported by the bridge framework and is configured to travel in a second direction 759 that is perpendicular to the first direction 761 and along the bridge framework. For example, another rotor 757-2 is coupled to the bridge framework. Rotation of the other rotor 757-2 moves the gantry head 756 in a direction perpendicular to the set of tracks. The bridge framework can include at least one arm that is coupled to the other rotor 757-2 and the gantry head 756 to cause movement of the gantry head 756 in the direction perpendicular to the set of track, e.g., the second direction 759.

As further illustrated and described herein, the gantry head 756 includes plurality of interface tools arranged on the gantry head and that are used to selectively provide a plurality of interactions with a biological sample at a plurality of locations within the portable container of the analyzer apparatus. The gantry head 756 can physically move to different locations between and outside of the set of tracks in two-dimensional or three-dimensional directions to provide the plurality of interactions, which are identified via the configuration information. In specific embodiments, the gantry can be referred to or form part of a mechanical subassembly or stimulator. The gantry, via the plurality of interface tools coupled thereto, is used to selectively output different types of energy outputs toward the biological sample to provide different interactions with the biological sample at a plurality of locations across the analyzer apparatus.

Figure 7C:
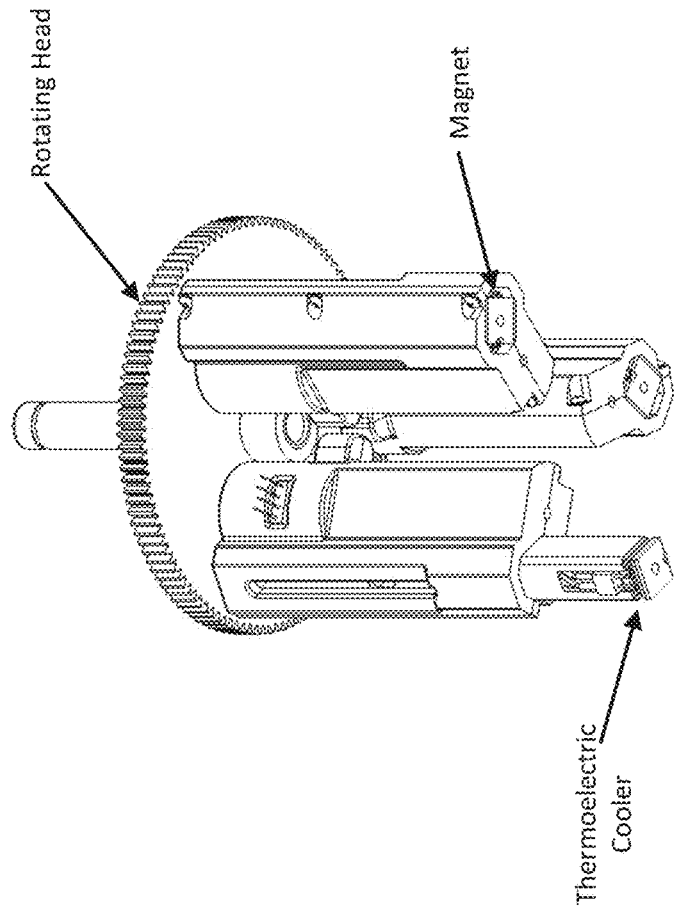

FIG. 7C illustrates a view of the gantry head of the gantry apparatus in accordance with various embodiments. The plurality of interface tools can be located about or around the periphery of the gantry head, such as located on the circumference of the gantry head. In such embodiments, the gantry head is rotatable, e.g., a rotating head, and used to provide one of the plurality of interactions with the biological sample by rotating the gantry head to align a respective interface tool with a particular location within the analyzer apparatus. As described above, example interface tools that can be coupled to the gantry head can include a heat source and/or a cooling source (e.g., TEC) to heat and/or cool the biological sample, a magnetic source to apply magnetic forces, an acoustic tool to apply acoustic forces, a motor, among various other tools. In various embodiments, the gantry head is detachable from the bridge framework. For example, the gantry head can be detached from the bridge framework and another gantry head, which may have a different set of interface tools, can be attached to the bridge framework.

Figure 7D:
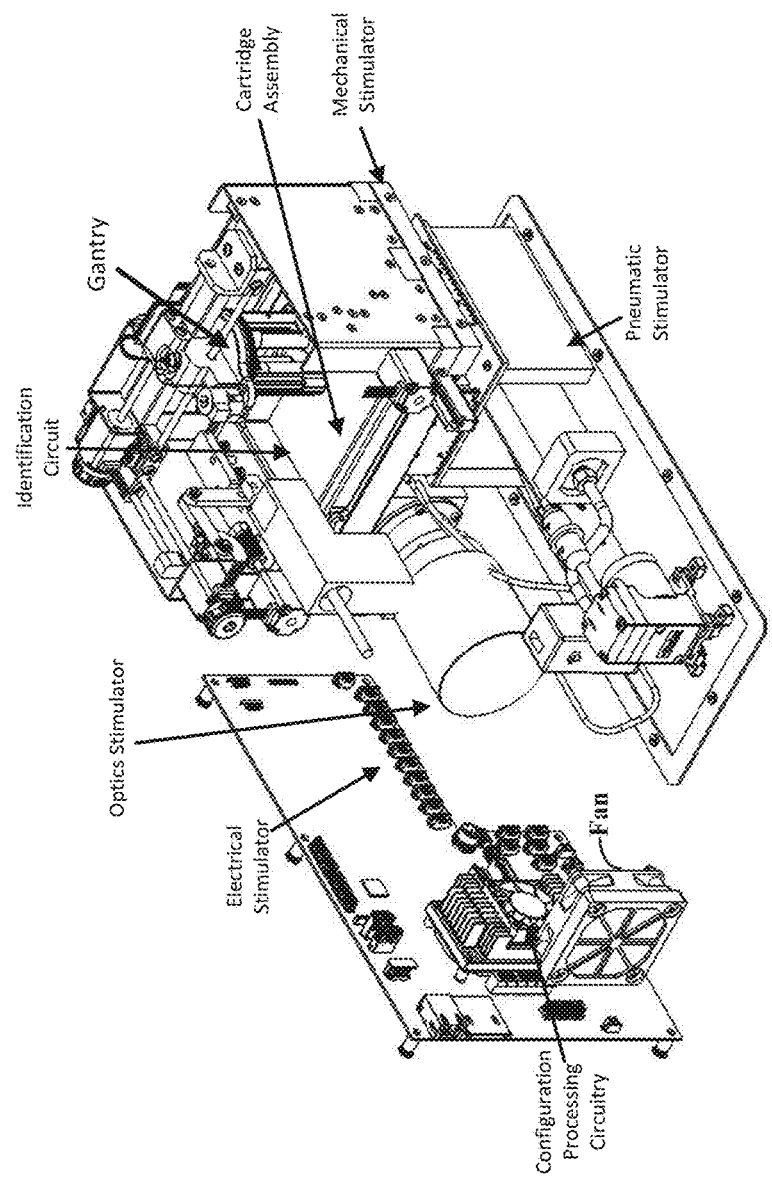

FIG. 7D illustrates an example of an analyzer apparatus that includes a gantry. As described above, the gantry can be enclosed by the analyzer apparatus. The gantry is used to provide a variety of interactions at different locations within the analyzer apparatus, which can allow for flexibility for physical interactions (e.g., heat, acoustics, magnetic) with the biological sample. The configuration processing circuit can instruct the gantry to provide the different interactions at the different locations and at corresponding times during processing of the biological sample. The gantry head can be pre-installed with a fixed set of capabilities, the interface tools can be detachable and different tools can be attached and/or the gantry head can be detachable from the bridge framework to provide additional field configurable capabilities.

As illustrated and previously described, the analyzer apparatus further includes a cartridge assembly for holding the sample processing cartridge, and the configuration processing circuitry and identification circuit to identify configuration information for the specific sample processing cartridge. The sample processing cartridge is loaded into the cartridge assembly and in response thereto, the analyzer apparatus configures itself for analyzing the specific biological sample. The configuration can include use of the different stimulators and/or interface tools of the gantry at different times, locations, and/or based on other interface parameters. As previously described, the stimulators include an optics stimulator, the gantry, an electrical stimulator, pneumatic stimulator, and optionally, additional mechanical stimulator.

In specific embodiments, the thermal stimulator, or a portion thereof (e.g., the TEC), can be part of the gantry, such as an interface tool of the gantry apparatus. The thermal stimulator provides temperature control at specific locations and times to enable the customized sample processing required by the sample-processing cartridge. The at least portion of the thermal stimulator (via the TEC) is movable by the gantry. Further, in specific embodiments, the optical stimulator includes a mechanical mechanism, such as a wheel that the digital microarray is placed on that rotate and/or that rotates the location of the light beam on the digital light beam. Such a mechanical mechanism can be an interface tool located on the gantry head of the gantry, in specific embodiments.

Figure 7E:
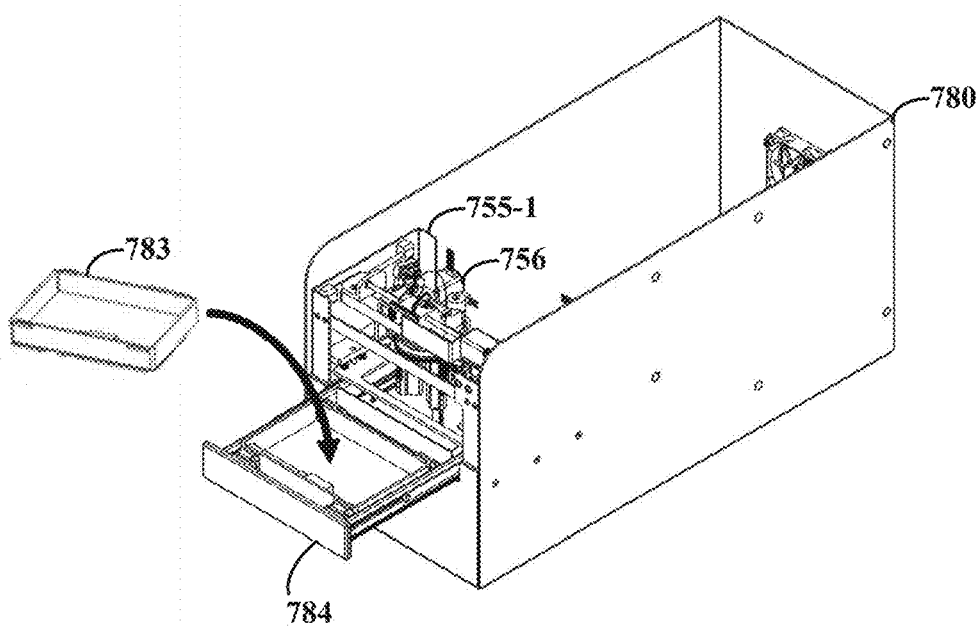
Figure 7F:
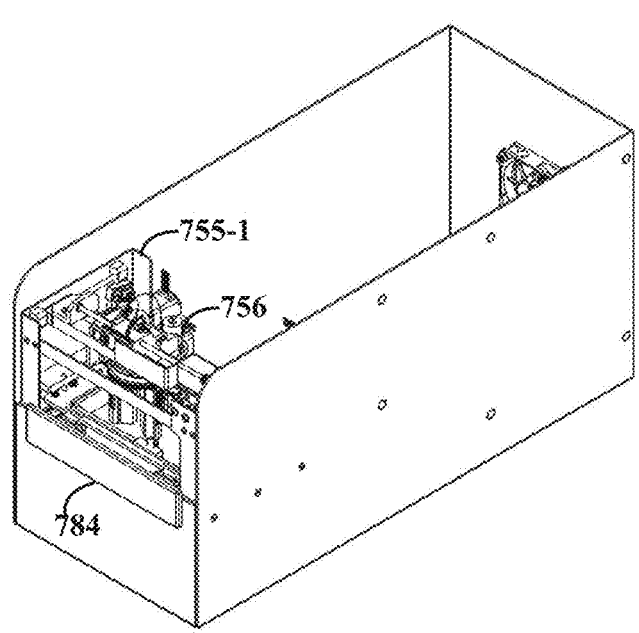

FIGS. 7E-7F illustrate a partial view of an analyzer apparatus including a gantry in accordance with various embodiments. As illustrated by FIG. 7E, the cartridge assembly 784 includes a tray that is configured to hold the sample-processing cartridge 783. The tray can move to multiple positions. For example, the tray can have and/or be moved by the analyzer apparatus to a first position in which the tray is located outside the analyzer apparatus 780 such that a user can place the sample-processing cartridge 783 within the tray, as illustrated by FIG. 7E. FIG. 7F illustrates a second position of the tray in which the tray is enclosed by the analyzer apparatus 780 and the analyzer apparatus configures itself for analyzing the biological sample contained therein. As is further illustrated by FIG. 7E-7F, the gantry is mounted to the analyzer apparatus 780 via brackets (e.g., bracket 755-1 is illustrated) and the gantry head 756 is coupled to a bridge framework and a set of tracks, and located proximal to the second position of the tray of the cartridge assembly 784. The sample-processing cartridge 783 can be loaded into the cartridge assembly 784 such that the top layer that contains the reagents module and other modules (e.g., top layer 442 illustrated by FIG. 4) is located proximal to the gantry head 756 (e.g., the top layer is facing upward).

Figure 7G:
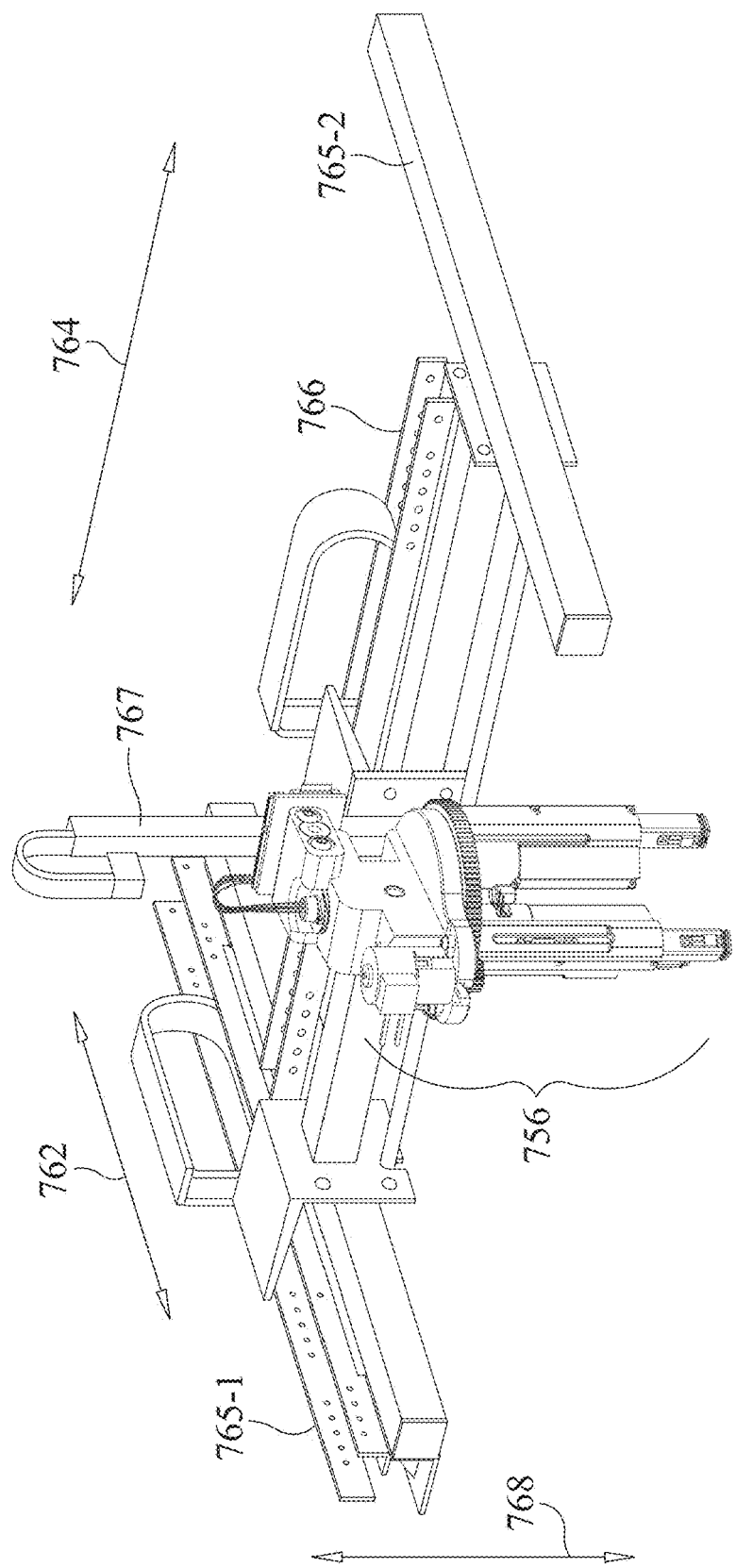
Figure 7H:
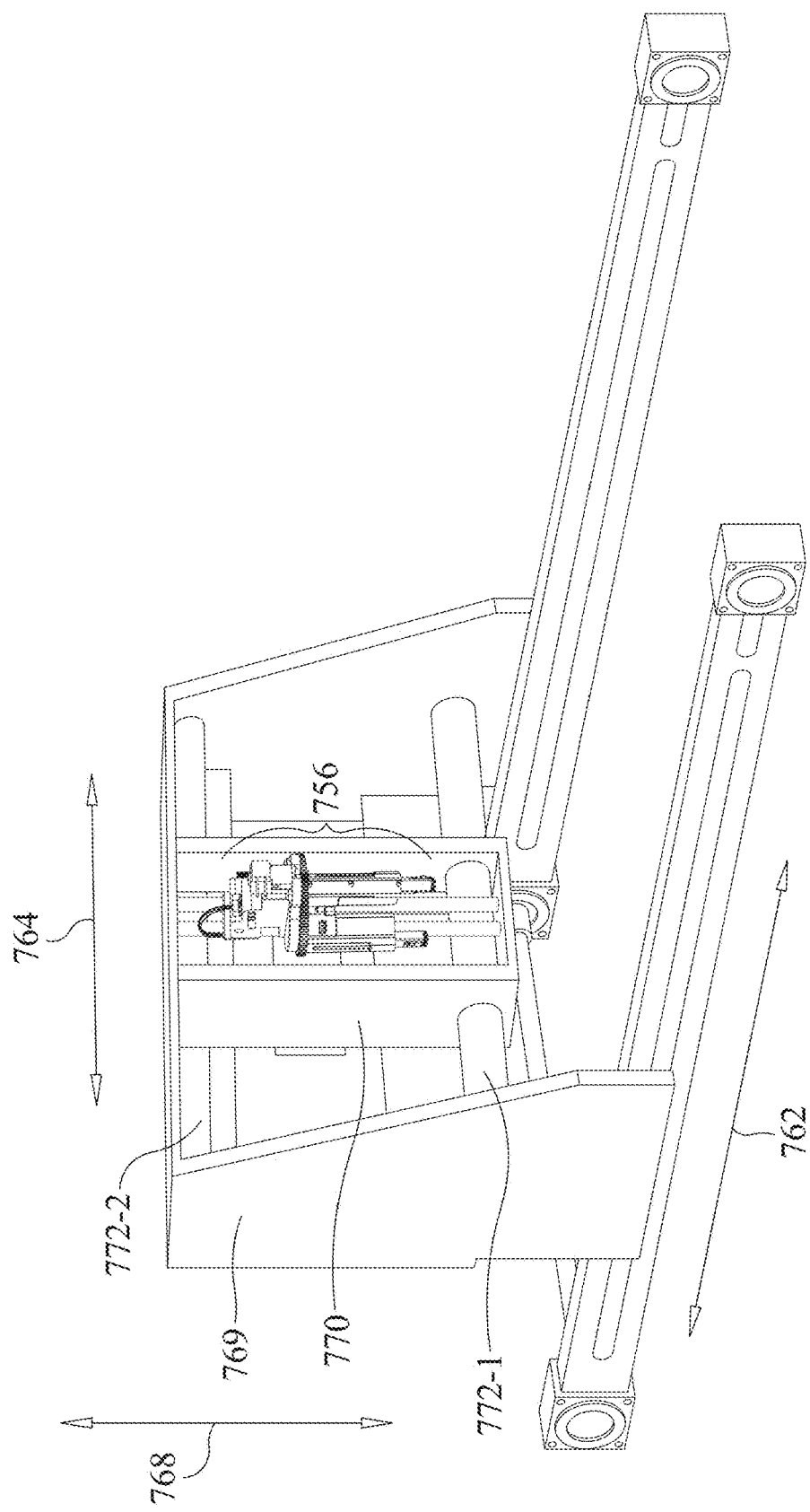
Figure 71:
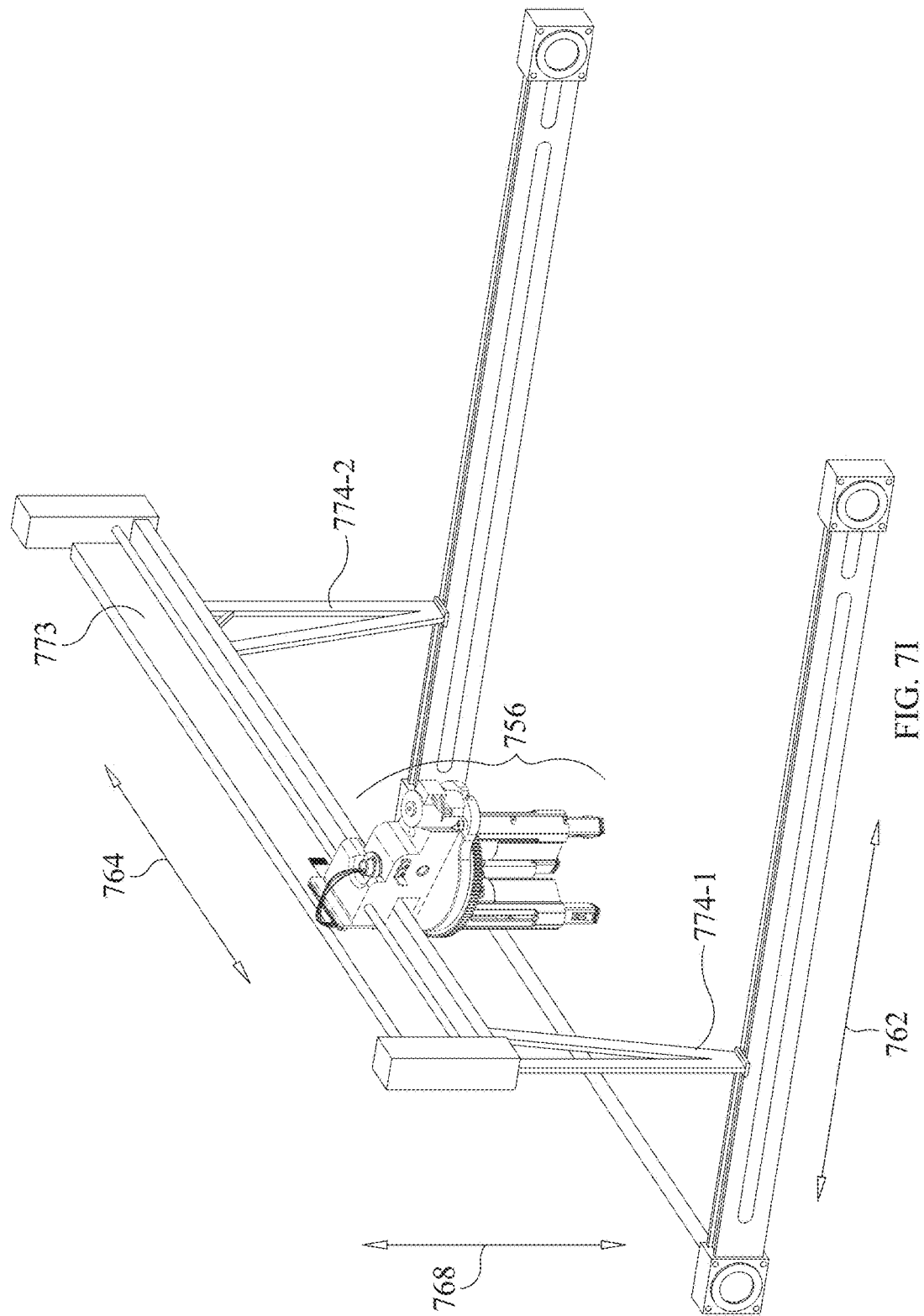

FIGS. 7G-7I illustrated different examples of specific gantry apparatuses, in accordance with various embodiments. The gantries illustrated by FIGS. 7G-7I can include the structural components used to provide the functional features as previously described in connection with the gantries illustrated by FIGS. 7A-7B, such as the previously described gantry head having a plurality of interface tools and which can be moved to a variety of locations inside and outside of a set of parallel tracks.

The gantries illustrated by FIGS. 7G-7I can provide the movement of the gantry head using a variety of mechanisms. For example, FIG. 7G illustrates an example of a gantry apparatus in accordance with various embodiments. As illustrated, the gantry apparatus includes a set of tracks 765-1, 765-2, a bridge framework 766, a vertical adjustment arm 767, and a gantry head 756. The set of tracks 756-1, 756-2 are arranged parallel to one another and the bridge framework 766 spans the set of tracks. For example, the bridge framework can be perpendicular to the set of tracks, although embodiments are not so limited and the bridge framework can be at a variety of angles to the set of tracks. The vertical adjustment arm 767 can be perpendicular to the bridge framework 766 and the set of tracks 756-1, 756-2. The vertical adjustment arm 767 can couple with the gantry head 756, and can allow the gantry head 756 to be moved up or down the length of the vertical adjustment arm (e.g., to be moved further away from the bridge framework or closer to the bridge framework, respectively), such as along the axis 768. The gantry, in specific embodiments and as further illustrated herein, is enclosed by the analyzer apparatus. The set of tracks can be parallel to one another and elongate in a first direction 762, such as along a width or a length of the analyzer apparatus. The bridge framework spans the set of tracks in a second direction 764 and can travel along the set of tracks in the first direction 762 that the set of tracks elongate in.

The gantry head 756 includes the plurality of interface tools arranged thereon. The gantry head can provide a particular physical interaction with the biological sample by rotating the gantry head to align a respective interface tool with a particular location, as further described herein. In specific embodiments, the gantry moves the gantry head to different locations that are between and outside the set of tracks in two-dimensional and/or three-dimensional directions (e.g., X and Y and/or X, Y, and Z) via movement of the bridge framework and/or gantry head. The different interface tools can include a thermal energy tool to heat or cool the biological sample (e.g., a TEC), a magnetic source to apply magnetic forces, an acoustic tool for applying acoustic tools, a motor, and various other tools.

FIG. 7H illustrates another example of a gantry apparatus in accordance with various embodiments. As illustrated, the gantry apparatus includes a first set of tracks, a bridge framework 769, a vertical adjustment arm 770, and a gantry head 756. The first set of tracks are arranged parallel to one another and the bridge framework 769 spans the set of tracks. For example, the bridge framework 769 can be perpendicular to the first set of tracks, although embodiments are not so limited and the bridge framework can be at a variety of angles to the first set of tracks. The bridge framework 769 can include a second set of tracks 772-1, 772-2 arranged parallel to one another and perpendicular to the first set of tracks, as illustrated. The vertical adjustment arm 770 can be coupled to the second set of tracks 772-1, 772-2 such that the vertical adjustment arm can move to different locations along the second direction 764 of the second set of tracks (e.g., from one side edge of the bridge framework to an opposing side edge of the bridge framework). The vertical adjustment arm 770 can also include a third set of tracks that are arranged perpendicular to both the first set of tracks and the second set of tracks, and which allow the coupled gantry head 756 to be moved up or down the length of the vertical adjustment arm such as along axis 768 (e.g., to be moved further away from the bridge framework or closer to the bridge framework, respectively). The gantry, in specific embodiments and as further illustrated herein, is enclosed by the analyzer apparatus. The first set of tracks can be parallel to one another and elongate in a first direction 762, such as along a width or a length of the analyzer apparatus. The gantry head includes the plurality of interface tools, as discussed herein. The gantry head can provide a particular physical interaction with the biological sample by rotating the gantry head to align a respective interface tool with a particular location, as further described herein.

FIG. 7I illustrates another example of a gantry apparatus in accordance with various embodiments. As illustrated, the gantry apparatus includes a set of tracks, a bridge framework 773, a set of adjustable brackets 774-1, 774-2, and a gantry head 756. The set of tracks are arranged parallel to one another and the bridge framework 773 spans the set of tracks. For example, the bridge framework 773 can be perpendicular to the set of tracks, although embodiments are not so limited and the bridge framework 773 can be at a variety of angles to the set of tracks. The bridge framework 773 can be adjustable via the adjustable brackets 774-1, 774-2, such that the bridge framework 773 is moved up or down along the axis 768. The gantry head 756 can be coupled to the bridge framework 773, such that the gantry head 756 can move to different positions along the bridge framework 773, such as along the second direction 764. Moreover, the set of adjustable brackets 774-1, 774-2 can move to different positions along the set of tracks, such as along the first direction 762. The gantry, in specific embodiments and as further illustrated herein, is enclosed by the analyzer apparatus. The set of tracks can be parallel to one another and elongate in a first direction 762, such as along a width or a length of the analyzer apparatus. The gantry head 756 includes the plurality of interface tools, as discussed herein. The gantry head 756 can provide a particular physical interaction with the biological sample by rotating the gantry head to align a respective interface tool with a particular location, as further described herein.

FIGS. 8A-8E illustrate examples of sample-processing cartridges, in accordance with various embodiments of the present disclosure. The sample-processing cartridge can include a board assembly with a plurality of chambers that are in fluidic connection and that are used to perform the hybridization of the probes to the targets in the sample, purification, and amplification (and optionally the hybridization of the amplicons to a substrate, such as a microarray), such as the rapid assay apparatus illustrated by FIGS. 8A-8C. In such an apparatus, relevant chambers and/or modules are in fluidic communication so as to pass the biological sample from one chamber/module to the next for operating on the biological sample according to the functionality relevant thereto, such as the hybridization to probes, target purification, and amplification. In other embodiments, one or more additional apparatuses can be used to perform the hybridization and amplification processes, such as various thermal cyclers. For example, the biological sample can be in fluidic movement through a plurality of chambers of a sample-processing cartridge.

As illustrated, the sample-processing cartridges have data 804 thereon, e.g., the barcode, radio frequency tag, and/or memory location, which is used to self-configure an analyzer apparatus for assisting in processing the biological sample contained within the sample-processing cartridge. The data 804 can include or provide a memory location to obtain configuration information used to identify various biochemical processes to be performed and the order for performing the biochemical processes, locations of the sample-processing cartridge associated with the biochemical processes, and various parameters (e.g., temperature, timing, volume, etc.) associated with each of the biochemical processes. As previously described, the sample-processing cartridge can additionally include a means for a user to configure the test performed thereon, such as a label for the user to mark and/or coded data read from the sample-processing cartridge (e.g., a QR code).

In various embodiments, although not necessarily illustrated by FIGS. 8A-8E, the sample-processing cartridge can include a location for the analyzer apparatus to mark and/or otherwise disable the sample-processing cartridge after processing is complete. For example, the analyzer apparatus can change a color of a thermal label or marker, burn a location of the sample-processing cartridge, and/or code data on the sample-processing cartridge to disable the sample-processing cartridge or otherwise indicate that the sample-processing cartridge has already been processed. The marking and/or disablement can prevent or mitigate an additional test from being performed on the sample-processing cartridge. As a specific example, the sample-processing cartridge can include a thermal label or marker. After processing the cartridge, the analyzer apparatus uses the thermal energy tool (or an optical tool) to change a color of the thermal label or marker. By changing the color, if the same sample-processing cartridge is inserted back into the analyzer apparatus, the analyzer apparatus recognizes that the sample-processing cartridge has already been processed and rejects the test (e.g., outputs error message such as indicating cartridge is already processed). As another specific example, after processing the cartridge, the analyzer apparatus burns a portion of the sample-processing cartridge, such as burning the location of the data so that the data cannot subsequently be read or burning a predetermined location that indicates the cartridge has been processed. The analyzer apparatus can use the thermal energy source or a laser to burn the sample-processing cartridge. In another embodiment, the analyzer apparatus may recode the data on the sample-processing cartridge after processing the cartridge.

Figure 8A:
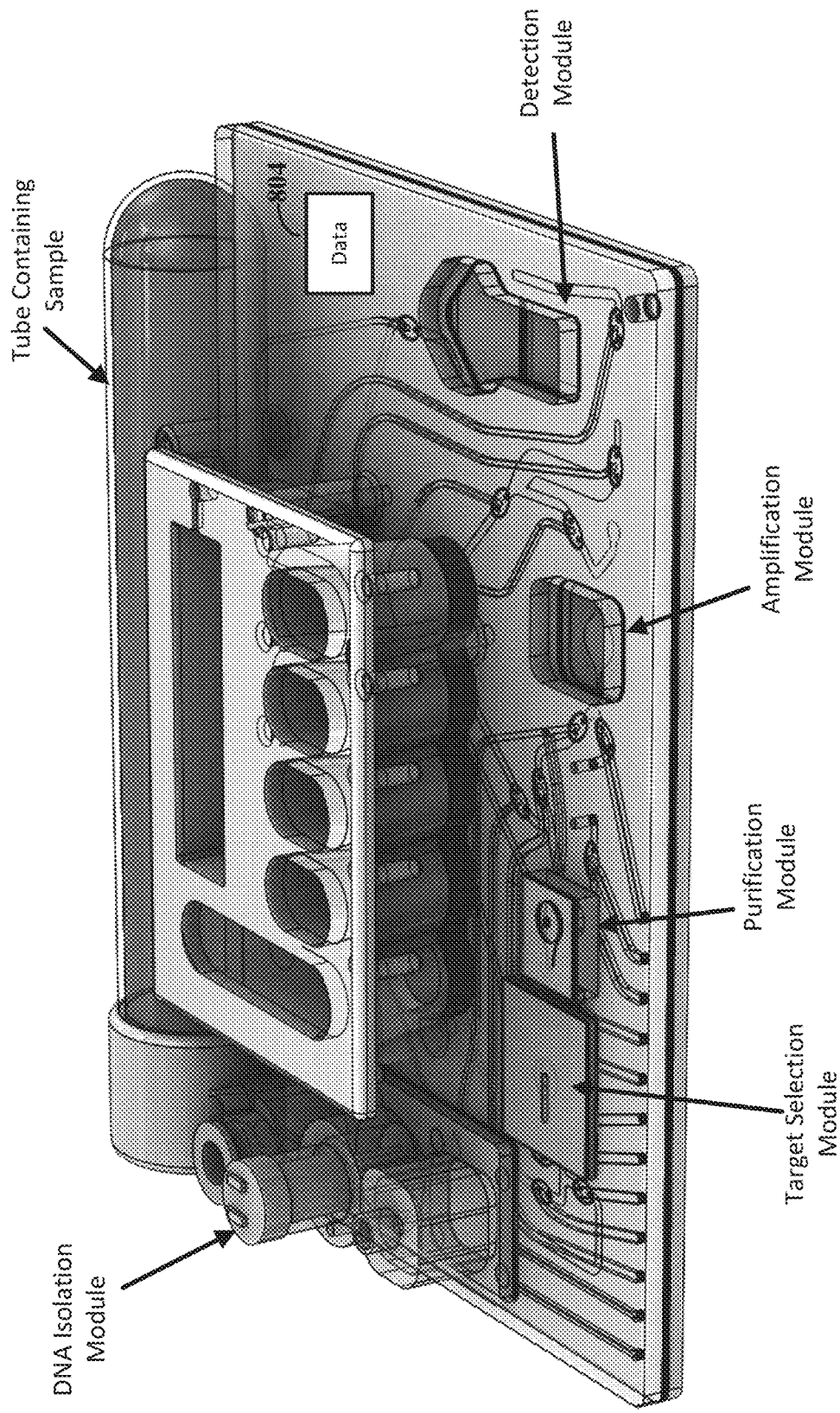

More specifically, FIG. 8A illustrates an example sample-processing cartridge used for analyzing cell free DNA. The sample-processing cartridge includes a plurality of biochemical processing modules that are self-contained on a board assembly. The board assembly includes fluid chambers and channels for processing a biological sample. In the specific embodiment illustrated by FIG. 8A, the biochemical processing modules includes a sample collection module connected to the blood tube containing the blood sample (e.g., plasma or serum), DNA isolation module, target purification module (which is also referred to herein as "a DNA extraction module"), target selection module, amplification module, and detection module. The sample-processing cartridge further includes the data 804 used to identify the configuration information and to configure the analyzer apparatus for a series of state configurations for processing the biological sample. For example, the configuration information can include spatial information identifying the locations of the respective modules, orders of processing the respective modules, biological-sample stimulators used to process the modules, and interface parameters at different times throughout the analysis.

FIG. 8B illustrates an example of a board assembly and FIG. 8C illustrates the separate biochemical processing modules. In various embodiments, the same board assembly can be used to form different sample-processing cartridges by connecting the respective biochemical processing modules used for processing the biological sample.

FIGS. 8D-8E illustrate other examples sample-processing cartridges. FIG. 8D illustrates an example cartridge used to analyze genomic DNA. The cartridge can include a swab elution module, a lysis module, a reverse transcription and PCR module, and detection module. FIG. 8E illustrates an example cartridge used to analyze mRNA. The cartridge can include a spore extraction module, purification module, PCR module, and detection module.

Embodiments are not limited to the sample-processing cartridges illustrated by FIGS. 8A-8E and can include a variety of commercially available cartridges, such as various microfluidic chips.

MORE SPECIFIC/EXPERIMENTAL EMBODIMENTS

Embodiments in accordance with the present disclosure include use of an analyzer apparatus to analyze and/or otherwise process different sample-processing cartridges. The analyzer apparatus is self-configurable for a plurality of different types of biological samples, mitigating manual configuration by a user, such as a laboratory technician, and which allows for the analyzer apparatus to be used for a variety of different analyses and processes. The different sample-processing cartridges can have different biochemical processing modules at different locations used to process different types of biological samples, such as genomic DNA, cfDNA, synthetic DNA, mRNA, miRNA, and other types of samples. The analyzer apparatus can be used in various experimental and/or more specific embodiments to analyze a specific biological sample contained within a specific sample-processing cartridge.

Figure 9:
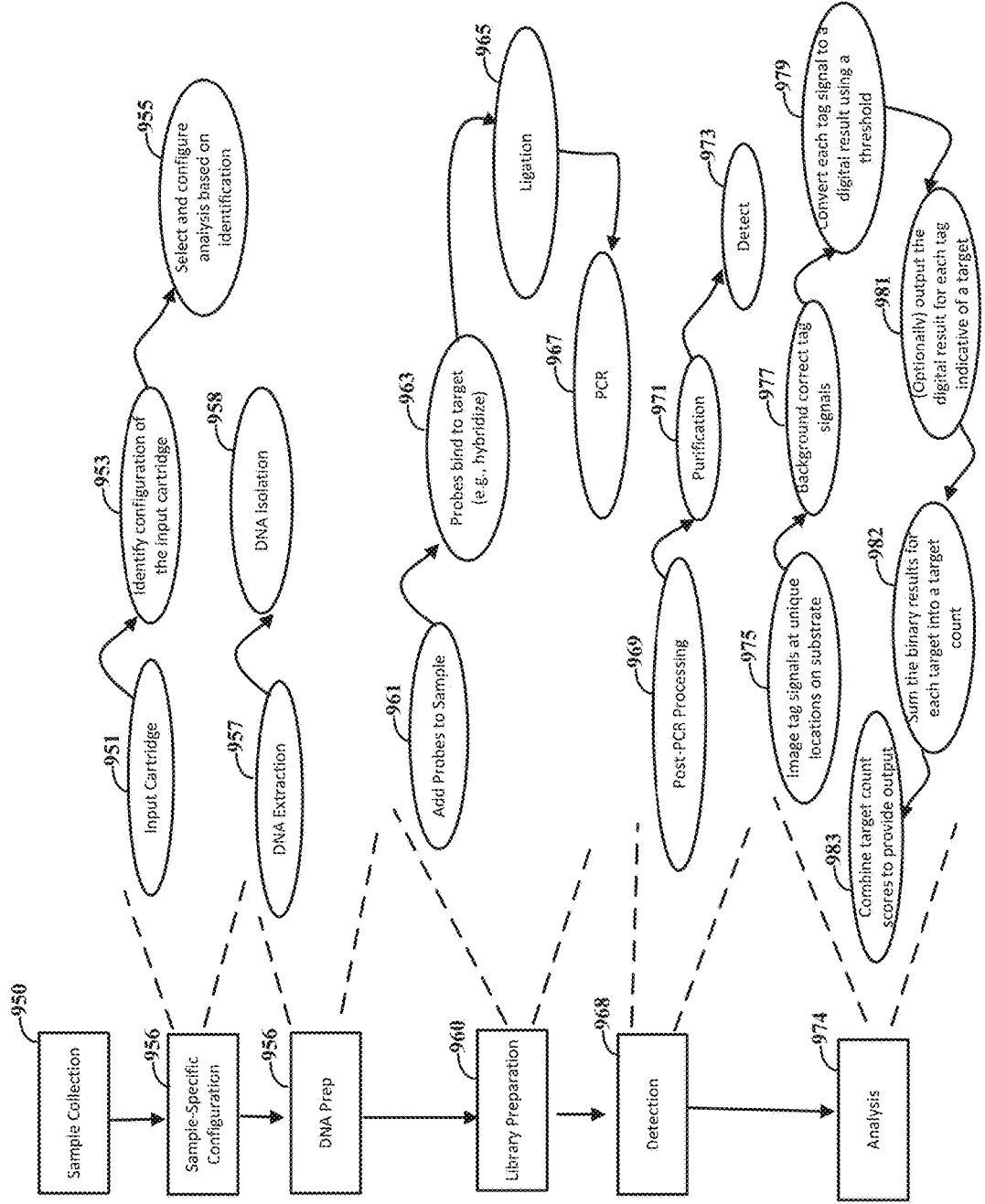
FIG. 9 illustrates an example method of using an analyzer apparatus for performing an analysis on a biological sample, in accordance with various embodiments of the present disclosure.

FIG. 9 illustrates an example method of using an analyzer apparatus for performing an analysis on a biological sample, in accordance with various specific and/or experimental embodiments of the present disclosure. A biological sample is collected from an organism, such as a human or other animal (although embodiments are not so limited and can include plant based samples) and placed in a sample-processing cartridge, at 950. The sample-processing cartridge can be configured for a particular analysis, at 956. For example, a plurality of different sample-processing cartridges can be available and used for different analysis. The user selects the particular sample-processing cartridge based on the process to be performed (e.g., end result intended). As previously described, the sample-processing cartridge can have data thereon that identifies the sample-processing cartridge. In various embodiments, the data can be used to automatically (e.g., without additional user input) configure the analyzer apparatus for the specific analysis to be performed. In other embodiments, the user may enter the data into the analyzer apparatus and/or external processing circuitry in communication with the analyzer apparatus and which is used to self-configure the analyzer apparatus.

As a specific example, the sample-specific configuration can include placing the sample-processing cartridge into the portable container of the analyzer apparatus, at 951. In response thereto, the analyzer apparatus identifies the data on the sample-processing cartridge and associated configuration information, at 953. Using the configuration information, the analyzer apparatus can self-configure itself for the particular analysis including the series of state configurations as described above, at 955.

Using the series of state configurations, an analysis of the biological sample is performed. FIG. 9 illustrates a specific analysis of DNA. For example, the series of configuration states can include DNA preparation at 959, library preparation at 960, detection at 968, and analysis at 974.

The DNA preparation at 959 can include DNA extraction at 957 and DNA isolation at 958 (e.g., lysis and bind). In a specific experimental embodiment, DNA extraction includes mixing the biological sample with enzymes and chemicals to release the DNA bound to proteins in the sample. In DNA extraction, example processing techniques involve the use of proteinase K, a detergent (such as tween-20), and/or chaotropic salts (such as guanidinium thiocyanate) and heat to activate the proteinase K. In accordance with various embodiments, the analyzer apparatus is configurable to engage a reagent block on the sample-processing cartridge (utilizing the gantry), to release liquid extraction reagents (utilizing the pneumatic stimulator), and move the sample to an extraction module (using the pneumatic stimulator). In the case of extraction, the gantry provides heat through the thermal stimulator (e.g., TEC) to the sample mixed with extraction chemistry to 56 degrees Celsius for 30 minutes and then cools the sample back to room temperature to move on to the purification step.

Once the DNA is extracted from bound proteins, the DNA is isolated from the rest of the plasma components (proteins, small molecules, lipids, etc.). Various approaches to DNA isolation include the use of silica frit spin columns or silica coated magnetic beads. In these approaches, the DNA can be bound to the silica frit by adjusting a chaotropic salt concentration while other biomolecules remain in solution. The DNA is isolated by washing with buffers (e.g. ethanol, isopropanol, low chaotropic salt buffers) to remove the biomolecules in solution. Finally, the DNA is eluted using a water buffer (e.g. Tris). In accordance with the present disclosure, the DNA is isolated using a mixing and binding chamber and a series of states as defined by the sample-processing cartridge at the sample run start. In one example, the sample-processing cartridge contains a mixing station and an embedded silica frit. The hardware state configures the pneumatic stimulator to deliver X M of guanidinium thiocyanate and Tween 20 to a final concentration of 5% to the biological sample in the mixing station (collectively the binding buffer). The mixing can be controlled by the analyzer apparatus using a number of different biological-sample stimulators: (1) creating turbulent flow using air bubbles (accomplished by the pneumatic stimulator), (2) the gantry can move a magnet around the chamber with magnetic beads in the chamber or (3) the gantry can use a motor to turn a paddle that is part of the mixing module. The biological sample and binding buffers are then flowed over a silica frit. The DNA is bound under conditions that are used commonly and well known by one of ordinary skill in the art. The frit is washed and then dried. The process of drying involves setting states that drive both air flow over the fit and heating from a TEC on the gantry. The biological sample is eluted using a Tris EDTA buffer. The gantry and thermal stimulator (e.g., thermal energy tool) provide variable elution temperatures to improve the yield of nucleic acid release of the DNA. The description above provides one example workflow of DNA isolation. As previously described, the DNA preparation can include one module or two separate modules used to respectively perform the extraction and isolation.

The library preparation, at 960, can include adding probes to the sample, at 961, and binding the probes to target DNA (e.g., hybridization), at 963. The probes, as would be appreciated, can be complementary to target sequences. The probes can be configured to bind to detection probes which may be bound to an array. For example, the detection probes can include a complementary sequence to the probes. As further described herein, in some embodiments, streptavidin solids supports are used to enable the capture of specific targets. The targets bound to the probes can then be ligated, at 965. For example, probes that annealed to the sample DNA are ligated together joining two probes that were previously independent molecules so that a single molecule includes both universal primer binding sites. The analyzer apparatus can provide pressure, flow control, magnetic forces, and heating, such as via the gantry and/or use of other biological-sample stimulators.

The bound targets are then amplified via a PCR process, at 967. During the amplification step, the analyzer apparatus can change configuration to provide hardware components to the location defined by the configuration processing circuit for amplification and controls the timing at each temperature state. In various embodiments, the PCR process includes universal PCR that uses universal PCR primers. As a specific example of a PCR process, the enzyme polymerase and deoxynucleoside trisphosphates (dNTPs) are added to the sample. Polymerase, such as Taq polymerase, is an enzyme that synthesizes nucleic acid molecules from deoxyribonucleotides. The dNTPs are the building blocks, e.g., the deoxyribonucleotides, from which polymerase synthesizes new DNA and/or RNA strands. Other components and reagents may be added, such as a buffer solution to provide a chemical environment that is suitable for activity and stability of polymerase, bivalent cations, magnesium, manganese ions, and/or potassium ions. The various components and/or reagents are added to the sample via movement of the biological sample through one or more chambers of the sample-processing cartridge, although embodiments are not so limited and can include the addition of components and/or reagents through other techniques.

The example PCR process includes repeated cycles of temperature changes. The cycling includes denaturation, annealing, and elongation. Denaturing can include heating the reaction to a first threshold temperature (e.g., 94-98 degrees Celsius) for a period of time, such as 20-30 seconds. Such denaturing causes nucleic acid melting by disrupting the hydrogen bonds between complementary bases and results in single-stranded nucleic acid molecules. The annealing operation can include heating the reaction to a second threshold temperature that is lower than the first threshold temperature (e.g., 50-65 degrees Celsius) for a period of time, such as 20-40 seconds. Such annealing causes the PCR primers to bind (e.g., anneal or hybridize) to the target. The elongation can include heating the reaction to a third threshold temperature which is dependent on the particular polymerase used, whether Taq polymerase or another suitable thermostable DNA polymerase. Using Taq, this polymerase can be optimally active at a temperature of 75-80 degrees Celsius and a temperature of 72 degrees may be used. During the elongation process, polymerase synthesizes a new nucleic acid strand complementary to the target by adding dNTPs that are complementary to the target in 5' to 3' direction, and condenses the 5'-phosphate group of the dNTPs with the 3'-hydroxyl group at the end of the nascent (extending) nucleic acid strand.

After the repeated cycles, a final elongation is performed. The final elongation includes heating the reaction to a fourth threshold temperature (e.g., 70-74 degrees Celsius or a value less than 90 degrees Celsius) for a period of time, such as 5-15 minutes. The final elongation process is used to ensure any remaining single-stranded nucleic acid sequence is fully extended. Optionally, after the final elongation, a final hold is performed. The final hold includes cooling the reaction to a particular temperature (e.g., 4-15 degrees Celsius). In various embodiments, the amplified reaction is stored within at the particular temperature. For example, the biological sample can be processed by the analyzer apparatus for subsequent analysis. In other specific embodiments, the amplicons are not stored, but rather analyzed immediately after the amplification process using the analyzer apparatus. As previously described, the library preparation can include one module or separate modules used to respectively perform the target selection and amplification. The gantry, thermal stimulator, and pneumatic stimulator (as well as the electrical stimulator) can be used to provide the various interactions described above, including the repeated cycles of temperature changes.

The amplicons are bound to the substrate, such as an array. The targets can be detected at 968 via post-PCR processing at 969, purification at 971, and detection at 973, such as via a detection module as previously describe. Various post-PCR processing can be performed including purification and detection at 968. In various embodiments, an analysis is done by hybridization to a substrate, such as a microarray. The analyzer apparatus controls the mixing of the sample and hybridization buffer in preparation for DNA hybridization using the pneumatic stimulator. In addition, the analyzer apparatus can control the optical and thermal stimulators. The protocol (e.g. hybridization time, temperature, imaging time, mixing) is defined by the sample-processing cartridge prior to the run and the analyzer apparatus is configured at the moment.

In some specific embodiments, the output can include an analysis of the quantification of targets, at 974. For example, a digital output is provided by analyzing the surface of the substrate. Fluorescent signals at unique locations of the substrate, and indicative of a tag sequence and associated target, are analyzed and/or imaged using the optical stimulator, at 975. The fluorescent signals are referred to as tag signals in FIG. 9. In response to detecting a tag signal, the intensity of the tag signal is background corrected using a background noise value and normalized, at 977. In various embodiments, the background corrected and normalized tag signal is compared to a threshold to convert the output to a digital result (e.g., 0 or 1, pass/fail, off/on) for each tag indicative of a target at, 979. The threshold includes a simple pass/fail threshold. Optional, the binary result is output for each unique location that is associated with a tag sequence indicative of a target being analyzed, at 981, the binary results are combined, at 982, and the target count scores are output, at 983. For more general information regarding quantifying targets and specific information relating to a digital output of quantified targets, references are made to PCT Application (Ser. No. PCT/US2017/024098), entitled "Apparatuses and Methods for Assessing Target Sequence Numbers," filed Mar. 24, 2017, which is fully incorporated herein by reference. Although embodiments are not limited to a digital output and can include a variety of substrate analyses.

FIG. 10 illustrates an example method of using an analyzer apparatus for performing an analysis on a biological sample, in accordance with various embodiments of the present disclosure. For example, FIG. 10 illustrates an example of analyzing cell free (cf)DNA in accordance with various specific and/or experimental embodiments. As illustrated cfDNA analysis can include DNA extraction at 1001, DNA isolation at 1003, biotinylation at 1005, probe anneal at 1007, ligation and streptavidin binding at 1009, universal PCR at 1011, quantification of targets at 1013, and analysis at 1015.

In some specific and experimental embodiments, the sample-processing cartridge illustrated by FIG. 8A is inserted into an analyzer apparatus illustrated by FIG. 2 which has a gantry as illustrated by 7A. As may be appreciated, embodiments are not so limited and a variety of sample-processing cartridges and analyzer apparatuses can be used. In response to insertion of the sample-processing cartridge illustrated by FIG. 8A into the analyzer apparatus, the sample-specific configuration circuitry of the analyzer apparatus (e.g., sample-specific configuration circuitry 218 illustrated by FIG. 2) identifies the data (e.g., data 804 illustrated by FIG. 8A) located on the sample-processing cartridge and uses the data to configure itself. The self-configuration includes a series of state configurations, as previously described, including identification of which biological-sample stimulators interact with the biological sample at particular times, as well as the positions in the portable container for the biological-sample stimulators at the different times. The positions are associated with locations of the biochemical processing modules of the sample-processing cartridge. The data on the sample-processing cartridge provides spatial location information of the specific biochemical processing modules (e.g., the purification, DNA isolation, target selection, amplification, and detection modules) self-contained in the sample-processing cartridge along with timing and or temperature information and identification of the selected biological-sample stimulators used for performing the analysis at the specific times.

The identified positions are used by the different biological-sample stimulators to interact with the biological sample at the correct locations of the sample-processing cartridge. In some embodiments, the pneumatic stimulator (e.g., pneumatic stimulator 222 illustrated by FIG. 2) can use the identified positions to send forces that control movement of the sample throughout the analysis or cause specific channels to be blocked using a pneumatic valve. As previously described, the pneumatic stimulator includes a pump, tubing and channels that sends forces toward the biological sample and constantly controls movement of the biological sample through the sample-processing cartridge based on the configuration information. The gantry can locate different interactive tools at any locations within the analyzer apparatus. More specifically, the gantry head is moved in x, y, and/or z directions to the different positions and based on identification of locations of the different biochemical processing modules of the inserted sample-processing cartridge.

As previously described, the sample-processing cartridge includes a plurality of biochemical processing modules. In an example experimental embodiment, the sample-processing cartridge includes, as illustrated by FIG. 8A, a purification module used to perform DNA preparation including DNA extraction at 1001 and DNA isolation at 1003, a target selection module and amplification module used to perform library preparation including (optionally) biotinylation at 1005, probe anneal at 1007, streptavidin binding and ligation at 1009 and universal PCR at 1011, and a detection module used to quantify targets at 1013 and analyze the targets at 1015. Each biochemical process module can include at least one chamber that is connected to other portions of the biochemical processing module (or other modules) by channels and valves. The pneumatic stimulator controls the flow of the biological sample and other reagents through the sample-processing cartridge. In the specific experimental embodiment, the purification module includes a lysis chamber, binding elements (e.g., beads or solid supports), a mixing chamber, and a TEC interface. The DNA isolation chamber can include one or more binding agent chambers configured to hold liquid reagents and selectively provide the reagents to chambers of the purification module. The target selection module can include one more chambers, lyophilized probes and enzymes, and a TEC interface. In specific embodiments, the target selection module includes a biotinylation chamber, a probe chamber, and a ligation chamber. In other embodiments, the target selection module includes a single library preparation chamber used to perform the library preparation. The amplification module includes an amplification chamber, lyophilized primers, enzymes and other reagents, and one or more TEC interfaces. The detection module includes a mixing chamber to prepare the biological sample for hybridization, a hybridization chamber having an assay, and interfaces to the TEC, optics, and laser.

The DNA extraction 1001 and DNA isolation 1003 can be used to perform DNA preparation. DNA preparation can be performed using multiple modules or a single module of the sample-processing cartridge. For example, as illustrated by FIG. 8A, the DNA extraction module is separate from the DNA isolation module. Although embodiments are not so limited and a purification module (e.g., such as the purification module 334 illustrated by FIG. 3) can be used to perform both DNA extraction and isolation. After inserting the sample-processing cartridge into the analyzer apparatus and configuring for analysis, the pneumatic stimulator moves at least a portion of the biological sample from a blood tube (or other input for the biological sample) to the one or more modules for DNA preparation. In a specific example, the pneumatic stimulator moves the portion of the biological sample from the blood tube to the purification module for DNA extraction followed by DNA isolation. For example, and as further described in the below specific experimental embodiment, 2 mL of plasma can be moved from a blood tube container that is holding 2.7 mL of plasma.

As previously described, DNA extraction at 1001 involves mixing raw plasma with enzymes and chemicals to release the cfDNA bound to proteins in the plasma within the purification module of the sample-processing cartridge. For DNA extraction, the pneumatic, electrical, and mechanical stimulators can be used. Typical processing techniques involve the use of proteinase K, a detergent (such as tween-20), and/or chaotropic salts (such as guanidinium thiocyanate) and heat to activate the proteinase K. In accordance with various embodiments, the analyzer apparatus is self-configurable to engage a liquid reagents module on the sample-processing cartridge (utilizing the gantry), to release liquid extraction reagents (utilizing the pneumatic stimulator), move the biological sample to the purification module (using the pneumatic stimulator), and mix solutions (using the magnetic or mechanical elements of the gantry, or the pneumatic stimulator). The purification module can include a mix chamber used for mixing the liquid extraction reagents with the biological sample. In some embodiments, the mix chamber has proteinase K located therein, and the detergent and/or chaotropic salts are released from the liquid reagents module (e.g., such as from a liquid reagents module 338 illustrated by FIG. 3) and moved to the purification module via use of the pneumatic stimulator. In other embodiments, each of the liquid extraction reagents, include proteinase K, are moved from the liquid reagents module. The gantry provides heat through the thermal stimulator (e.g., the TEC) to the biological sample mixed with extraction chemistry to 56 degrees Celsius for 30 minutes and then cools the biological sample back to room temperature to move on further processing and purification. For example, the gantry moves the gantry head in an x, y, and/z direction to position the gantry head and a respective heat source at a location of or associated with the purification module and provides the heat (e.g., 56 degrees Celsius) for the respective amount of time and at the particular time.

Once the DNA is extracted from bound proteins, at 1003, the DNA is isolated from the rest of the plasma components (proteins, small molecules, lipids, etc.). As noted above, a DNA isolation module can be used to perform DNA isolation. The DNA isolation module includes different liquid reagent chambers and/or bead elements. For example, the biological sample, which includes the extracted DNA mixed with the liquid extraction reagents, is moved from the mix chamber to one or more other chambers for isolating the DNA (e.g., mixing and/or binding chambers which are part of the purification module). The biological sample with liquid extraction reagents is moved via the pneumatic stimulator. While, after, and/or before moving the biological sample, the gantry can also move the gantry head to a position near the other chambers by moving the gantry head in an x, y, and/or z direction. Well described approaches to DNA isolation include the use of silica frit spin columns or silica coated magnetic beads. In these approaches, the DNA is preferentially bound to the silica by adjusting a chaotropic salt concentration while other biomolecules remain in solution. The DNA is isolated by washing with buffers (e.g. ethanol, isopropanol, low chaotropic salt buffers) to remove the biomolecules in solution. Finally, the DNA is eluted using a water buffer (e.g. Tris).

In a specific experimental example, the purification module contains a (binding) chamber having an embedded silica frit. Although embodiments are not so limited and other types of binding elements can be used. The state configurations can include the pneumatic stimulator delivering X M of guanidinium thiocyanate (GTC) and Tween 20 to a final concentration of 10% to the biological sample in the mixing chamber (collectively, the binding buffer). In the above-described specific embodiment, the solution of plasma and proteinase K are mixed with isopropanol and additional GTC and then flowed to the binding chamber having the embedded silica frit. While in the binding chamber, the solution is washed with different buffers (wash and ethanol), then dried and eluted using the elution.

The mixing can be controlled by the analyzer apparatus using a number of different biological-sample stimulators to: (1) create turbulent flow using air bubbles (accomplished by the pneumatic stimulator), (2) the gantry can move a magnet around the chamber with magnetic beads in the chamber or (3) the gantry can use a motor to turn a paddle that is part of one or more of the chambers. The gantry head, which may be located at a position associated with the location of the purification module, can rotate to utilize different interface tools used to provide different interactions with the biological sample. The biological sample and binding buffers are then flowed over a silica frit. The DNA is bound under conditions that are used commonly and well known by one of ordinary skill. The frit is washed and then dried. The process of drying involves setting states that drive both air flow over the frit using the pneumatic stimulator and heating from a TEC on the gantry using a heat source (e.g., rotating the gantry head to position the heat source relative to the frit). Finally, the biological sample is eluted using a Tris EDTA buffer via the pneumatic stimulator which drives (e.g., air) the buffer to the respective chamber. The mechanical and thermal stimulators provide variable elution temperatures to improve the yield of nucleic acid release of the DNA. Optionally, embodiments can utilize solid-phase reverse immobilization (SPRI) to bias the purified DNA for specific lengths. The pneumatic simulator moves the sample to magnetic beads held in a chamber which mixes the sample with the beads. The beads are captured using a magnet on the gantry to enable the pneumatic stimulator to empty the chamber of the binding solution and provide multiple solutions of different polyethylene glycol and ethanol percentages in order to bias the washing of different DNA fragment lengths. Finally, the gantry stimulator collects the beads while the pneumatic stimulator empties the chamber and introduces an elution buffer. The DNA sample is eluted from the bead by a TEC on the gantry as directed by the data encoded in the consumable cartridge. The DNA is then moved by the pneumatic simulator to prepare the library for targeted sequence analysis.

After the DNA preparation, the library can be prepared. Library preparation can include use of a target selection module and an amplification module of the sample-processing cartridge. For example, after extracting and isolating the DNA, the biological sample is moved to the target selection module via the pneumatic stimulator. In many typical library approaches, streptavidin solids supports are used to capture specific reagents. In the case of cfDNA purification, a streptavidin support can be used to capture the cfDNA after it has been biotinylated by a biochemical terminal transferase enzyme, at 1005. The thermal stimulator and gantry provide the conditions to carry out the biochemical reaction, while the pneumatic stimulator provides the movement of the biological sample to the biotinylation chamber. For example, the biological sample (which has various liquid reagents added) is moved from the purification module to the target selection module. The target selection module includes a biotinylation chamber having reagents for performing biotinylation, such as biotin and terminal deoxytransferase. The gantry head can rotate to locate the heat source proximal to the biotinylation chamber and to heat the mixture (such as to 37 degrees for sixty minutes). The solution is then mixed with probes for annealing. After annealing with probes, at 1007, the mixture containing the biological sample is moved and captured on a streptavidin solid support in a ligation chamber via the pneumatic stimulator. The target selection module can include the chamber for performing biotinylation and/or the probe chamber having the streptavidin solid support. The solid support can isolate the cfDNA in multiple ways, such as magnetic beads coated with streptavidin or flow through filters functionalized with streptavidin. The ligation chamber can include the solid support and primers, although embodiments are not so limited and the solid supports and primers can be moved into the probe chamber to mix with the biological sample. The gantry head, which is located at the target selection module and/or specifically at the probe chamber can be used to heat the probe chamber (e.g., 70 Celsius for 2 minutes and 35 Celsius for 2 hours), and liquid reagents are brought into the probe chamber from the liquid reagents module 338 (such as, LS wash and HS wash) using the pneumatic stimulator 222. The gantry head can then rotate to locate a magnetic source proximal to the probe chamber, and uses the magnetic source to mix the different liquids in the probe chamber.

Next the probes that are annealed to the sample DNA are ligated together joining two probes that were previously independent molecules so that a single molecule now includes both universal primer binding sites, at 1009. In these examples, the analyzer apparatus provides pressure, flow control, magnetic forces, and heating. The ligation can occur by the gantry head providing a series of interactions with the biological sample and various liquid reagents. In some embodiments, the target selection module includes a ligation chamber, although embodiments are not so limited and one or more of the biotinylation chamber, the probe chamber, and ligation chamber are a single chamber. The mixture, which includes DNA bound to the streptavidin support (or other solid support(s)) and primers) is moved to the ligation chamber using the pneumatic stimulator 222. The gantry head is also moved to a position associated with (or already is located at the position) the ligation chamber to provide various interactions with the biological sample. For example, the gantry head can heat the biological sample and various liquid reagents, liquid reagents are brought into the ligation chamber from the liquid reagents module 338 (such as, HS wash and elution wash) using the pneumatic stimulator, a magnetic source is used to mix the different liquids in the ligation chamber, the mixture is heated using the heat source, and the magnetic source is again used to mix the mixture. In the above-described specific embodiment, the solution containing DNA bound to the solid support and probes in the ligation chamber is washed and eluted. Elution can be accomplished chemically (NaOH) or thermally (denaturing the double stranded DNA above the ligated product melting temperature).

The mixture is then flowed to the amplification module, which includes an amplification (e.g., PCR) chamber and probes, enzymes and various reagents. Universal amplification and labeling of the annealed biological sample utilize both thermal and mechanical stimulators with sample movement controlled by the pneumatic stimulator, at 1011. During the amplification step, the analyzer apparatus changes configuration to provide the different biological-sample stimulators to the location defined by the configuration processing circuit for amplification and controls the timing at each temperature state. The amplification can include repeated cycles of different temperatures, e.g., PCR, as would be well understood by one of ordinary skill. The gantry head can provide the different temperatures and for the particular amount of time at the amplification chamber. In the above-described specific embodiment, the solution containing DNA eluted from the solid support is mixed with PCR mixture.

Although the above describes various different chambers used for the library preparation, in some embodiments, the library preparation includes use of a target selection module and an amplification module. The target selection module includes a first chamber in which the biological sample (as extracted and isolated) is mixed with a solid structure, oligonucleotide probes and various reagents to anneal the isolated DNA targets to the solid structures and probes (e.g., biotinylation, probe anneal, and ligation). Various liquid reagents are brought to the first chamber via the pneumatic stimulator. The amplification module includes an amplification chamber, as described above, which is used to perform PCR by mixing the bound target DNA with a PCR mixture and performing the amplification using the pneumatic stimulator and gantry.

The amplified DNA targets are then moved to a detection module of the sample-processing cartridge via the pneumatic stimulator for sequence analysis. The gantry head can additionally be moved to a position associated with the detection module. The sequence analysis can be performed by hybridization of the targets to a (DNA) microarray. For example, the solution is flown to a mixing chamber for preparing the biological sample for hybridization. The analyzer apparatus controls the mixing of the biological sample and hybridization buffer, such as SSPE, in preparation for DNA hybridization using the pneumatic stimulator. The prepared solution is then flowed to a hybridization chamber that has an assay, such as a microarray, for hybridizing to the assay and for detection of the targets. The hybridization assay can be heated to assist in the hybridization. The analyzer apparatus can control the optical and thermal stimulator for performing the hybridization and subsequent detection. The protocol (e.g. hybridization time, temperature, imaging time, mixing) is defined by the sample-processing cartridge prior to the run and the analyzer apparatus is configured at the moment which can be used to quantify targets, at 1013, and perform analysis on the results, at 1015. The detection module can include, in the specific example, a mixing chamber having hybridization buffer and the hybridization chamber having the (DNA) microarray (although embodiments are not so limited), and the pneumatic stimulator is used to move the mixture from the mixing chamber to the hybridization chamber.

Although the above FIG. 10 describes a particular example, embodiments are not limited to the specific liquid reagents, chambers, temperatures, and/or amounts of reagents/liquids. The reagents, in further specific embodiments, can be frozen and/or lyophilized.

The following is a specific example of processing a biological sample using the analyzer apparatus as illustrated by FIG. 2 in accordance with various embodiment and the sample-processing cartridge illustrated by FIG. 8A. In the specific example, the pneumatic stimulator (e.g., the pneumatic stimulator 222 illustrated by FIG. 2) moves 2 mL of the biological sample from the plasma tube to the purification module for DNA extraction and DNA isolation. For example, 2 mL of plasma is mixed with 0.58 mL of lysis reagents including proteinase K in the lysis chamber and then flowed to a binding chamber. In the binding chamber, the 2.58 mL solution of plasma and proteinase K are mixed with 2.0 mL of a GTC and tween-20 (forming 4.58 mL solution in the binding chamber) and then flowed to the mixing chamber having the embedded silica frit. While in the mixing chamber, the solution is washed with different buffers (750 uL wash and 750 uL ethanol), then dried and eluted using the elution to form 20 uL of solution. The 20 uL solution is then flowed to library preparation module.

The solution, now 20 uL, is then flown to the target selection module. More specifically, the 20 uL solution is flown to the biotinylation chamber and mixed with 1 uL of biotin and heated to 37 degrees for 60 minutes to form a solution of 21 uL. The 21 uL solution is then flown to a probe chamber (or optionally all performed in a single chamber) having the streptavidin solid support and probes, and is washed with 75 uL wash and 75 uL HS wash to form a solution of 21 uL. The 21 uL solution is then flown to the ligation chamber (in various optional embodiments, the biotinylation chamber, the probe chamber, and ligation chamber are a single chamber). The solution in the ligation chamber is heated to 45 degrees Celsius for 30 minutes, liquid reagents are brought into the ligation chamber from the liquid reagents module (e.g., the liquid reagents module 338 illustrated by FIG. 3), such as, HS wash and elution wash, using the pneumatic stimulator, and a magnetic source is used to mix the different liquids in the ligation chamber. The solution is then heated to 95 degrees for 2 minutes using the heat source, and the magnetic source is again used to mix the solution. The ligation process can form a solution of 25 uL. The 25 uL solution is then moved to an amplification chamber of the amplification module and PCR is performed. For example, the ligated probes and primers are mixed with 1 uL of PCR mixture to form a 26 uL solution, which is brought through repeated cycles of different temperatures.

The amplified DNA targets are then flown to the detection module. For example, the solution containing the amplified DNA targets is flown to the mixing chamber of the detection module and mixed with hybridization buffer, such as SSPE. The solution is then directed to the hybridization chamber having the microarray and heated to assist in hybridization using the heat source of the gantry. The detection module includes interfaces for the optical stimulator, such as optic and laser interfaces, and which are used to detect targets bound to the microarray.

The above described example is a specific experimental embodiment and various embodiments in accordance with the present disclosure can include a variety of variations. Some variations, as described above, can include different sample-processing cartridges having different numbers or types of biochemical processing modules. Further, the biochemical processing modules can include different chambers and flow methods. For example, the reagents can be liquid, solid, frozen and/or lyophilized. The reagents can be located in a chamber of the biochemical processing module and the sample is moved to the chamber. In other embodiments and/or in addition (at a different biochemical step), reagents can be located in a first chamber of the biochemical processing module or the liquid reagents module and can be moved to a second chamber that the sample is located in. For DNA preparation, other various embodiments include combining the lysis chamber with the binding chamber and/or mixing chamber, combining the binding and mixing chamber into a single binding chamber, using a bind solution for wash, and/or using beads as the solid support. Targets that are analyzed are not limited to cfDNA, and can include gDNA, mRNA, miRNA, and other nucleic acid targets, as well as non-nucleic acid targets, such as synthetic DNA coupled to an antibody.

FIG. 11 illustrates an example method of using an analyzer apparatus for performing an analysis on a sample, in accordance with various embodiments of the present disclosure. For example, FIG. 11 illustrates an example of analyzing cell messenger RNA (mRNA) in peripheral mononuclear cells (PBMCs). The consumable cartridge provides information to the hardware system, e.g., the configuration processing circuitry as illustrated in FIG. 7D, to enable remote programming of the hardware system states to provide for analysis of mRNA in multiple samples. The illustrative embodiment described below is for mRNA and can be used to diagnosis infections, inflammatory disease (e.g. lupus), and certain cancers. In such embodiments, a sample of whole blood is lysed to extract the mRNA and other nucleic acids from their cellular compartments, at 1121. The RNA is isolated from the sample using one or more of a variety of methods, at 1123, including the solid phase extraction and poly-A binding for mRNA specific isolation.

Other approaches well known to those skilled in the art. After the isolation, in some embodiments, the mRNA is separated from the total RNA which includes both tRNA and rRNA, at 1125.

Figure 12:
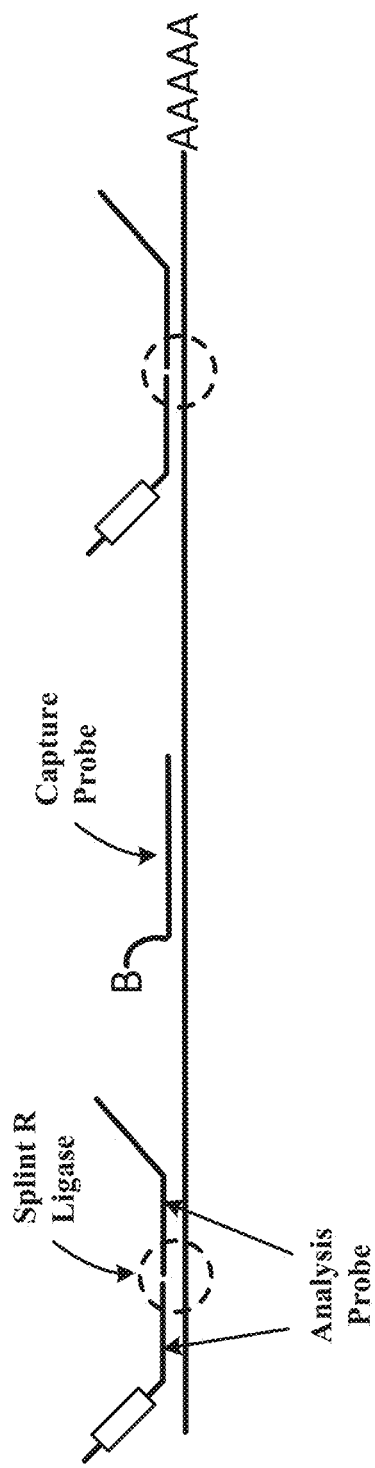
FIG. 12 illustrates a ligase that is active on DNA:RNA hybrid, in accordance with various embodiments.

One example approach to mRNA purification is using a capture probe labeled with a separation molecule (e.g. biotin), as shown in FIG. 12, which is subsequently bound to a solid support using a streptavidin interaction. The capture probe can be designed to cover splice junctions or can be a poly-T nucleic acid that hybridizes to the poly-A tail that is unique to mRNA transcripts. The hybridized DNA probe: RNA target binds to a solid support using the separation molecule interactions while the remaining nucleic acids are washed away. In embodiments that the capture probe is a poly-T oligonucleotide, (all) the mRNA are captured and the analyzer apparatus and analysis software can support development applications. In the instance where the capture probe is for specific transcripts, the resulting analysis may be only for those specific transcripts.

Once the mRNA is captured, at 1127, in specific embodiments, analysis probes are annealed to the remaining transcripts. The analysis probes are designed to specifically target different mRNA transcripts. In some embodiments, only a single analysis probes set may target a specific transcript sequence or multiple different analysis probes can be used to provide a signal amplification. The target probes contain universal PCR primers and tag sequences for analysis on a DNA microarray. The analysis probes are linked using a ligase.

FIG. 12 illustrates a ligase that is active on DNA:RNA hybrid, in accordance with various embodiments. However, embodiments are not so limited and other embodiments can include converting the mRNA transcript to complementary DNA using a reverse transcriptase and then using standard DNA:DNA ligase to link the two analysis probes, such as at 1129.

After ligation, e.g., at 1129, is complete the analysis probes are separated from the target transcript using one or more of multiple methods. In one example method, heating the solution above the melting temperature of the ligated analysis probe can elute the probe from the solid support and the transcript. As described above in the cfDNA implementation, the ligated probes are amplified together in single reaction pool based on the universal primers, at 1131.

The amplified DNA targets are then flown to the detection module. For example, the solution containing the amplified DNA targets is flown to the mixing chamber of the detection module and mixed with hybridization buffer, such as SSPE. The solution is then directed to the hybridization chamber having the microarray and heated to assist in hybridization using the heat source of the gantry. The detection module includes interfaces for the optical stimulator, such as optic and laser interfaces, and which are used to detect targets bound to the microarray for quantifying the targets 1133 and further analysis at 1135 as previously described.

Various embodiments are implemented in accordance with patent documents as previous described and identified, and which are fully incorporated by reference. For information regarding details of these and other embodiments, applications and experiments (as combinable in varying degrees with the teachings herein), reference may be made to the teachings and underlying references provided in the patent documents which form part of this patent document and is fully incorporated herein. Accordingly, the present disclosure is related to methods, applications and devices in and stemming from the disclosures in the patent documents and also to the uses and development of devices and processes discussed in connection with the references cited herein.

Certain embodiments are directed to a computer program product (e.g., nonvolatile memory device), which includes a machine or computer-readable medium having stored thereon instructions which may be executed by a computer (or other electronic device, such as processing circuitry or the detection circuitry) to perform these operations/activities.

Various embodiments described above may be implemented together and/or in other manners. One or more of the items depicted in the present disclosure can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

Based upon the above discussion and illustrations, those skilled in the art will readily recognize that various modifications and changes may be made to the various embodiments without strictly following the exemplary embodiments and applications illustrated and described herein. As an example, the processing circuitry and the detection circuitry can be part of separate devices and in communication via a wireless or wired link or can be part of the same device. Such modifications do not depart from the true spirit and scope of various aspects of the invention, including aspects set forth in the claims.

What is claimed is:

1. An analyzer apparatus for use with a sample-processing cartridge, the analyzer apparatus comprising:
   a plurality of biological-sample stimulators configured and arranged to emit energy, thereby causing interactions with a biological sample, wherein the plurality of biological-sample stimulators include:
      a gantry having a plurality of interface tools arranged about a gantry head, the plurality of interface tools including a magnet, a cooling source or heating source, and a motor, wherein the gantry head is movable in at least two-dimensional directions and is rotatable;
      a pneumatic stimulator including a pump, tubing and channels; and
      an optical stimulator, including a light source and a detector, including circuitry;
   sample-specific configuration circuitry configured to selectively control the plurality of biological-sample stimulators of the analyzer apparatus;
   a container configured and arranged to accept the sample-processing cartridge having the biological sample therein, wherein the sample-specific configuration circuitry and the plurality of biological-sample stimulators are contained with the container; and
   the sample-specific configuration circuitry including a memory circuit configured to store and access configuration information specific to the sample-processing cartridge, the configuration information including data indicative of a configuration of the sample-processing cartridge, the sample-specific configuration circuitry further including a configuration processing circuit configured to configure the analyzer apparatus, based on the configuration information, for a series of state configurations associated with different positions of the gantry and selective control of the plurality of biological-sample stimulators by:

selecting which of the plurality of biological-sample stimulators to emit the energy toward the sample-processing cartridge, as accepted by the analyzer apparatus, at a plurality of different times specific to an analysis of the biological sample and based on the series of state configuration;

identifying the different positions in the container for the gantry associated with at least a subset of the plurality of different times based on the series of state configuration; and performing biochemical processing on the biological sample using the selected ones of the plurality of biological-sample stimulators at each of the plurality of different times.

2. The analyzer apparatus of claim 1, wherein:

the pneumatic stimulator including the pump, tubing and channels, is configured and arranged to send forces toward the biological sample and thereby control movement of the biological sample through the sample-processing cartridge;

the gantry is configured and arranged to selectively move the gantry head and emit the energy, toward the biological sample, the plurality of interface tools including:

the magnet configured and arranged to apply magnetic forces; and the heat source or cooling source configured and arranged to transfer thermal energy toward or from the biological sample and thereby provide temperature control at specific locations and time; and the analyzer apparatus further including electrical circuitry configured and arranged to output electrical timing signals for controlling actions performed by the plurality of biological-sample stimulators.

3. The analyzer apparatus of claim 1, wherein the optical stimulator, including the light source and detector, including the circuitry, is further configured and arranged to output an optical signal toward the biological sample and capture image data of the biological sample responsive to the optical signal.

4. The analyzer apparatus of claim 1, wherein the sample-specific configuration circuitry includes:

an identification circuit configured to identify the sample-processing cartridge by scanning data located on the sample-processing cartridge and identify the configuration information using the data; and the configuration processing circuit is further configured to process the configuration information accessed from the memory circuit and provide the series of state configurations using the processed configuration information.

5. The analyzer apparatus of claim 1, wherein the sample-specific configuration circuitry is further configured to identify the configuration information specific to the sample-processing cartridge by scanning or reading data stored as a barcode or in a radio frequency tag on the sample-processing cartridge, wherein the data indicates a cloud-based location and wherein the sample-specific configuration circuitry further includes a communication circuit configured to download the configuration information from the cloud-based location and store the configuration information on the memory circuit.

6. The analyzer apparatus of claim 1, wherein the sample-specific configuration circuitry configures the analyzer apparatus for the series of state configurations by providing spatial location information of specific biochemical processing modules forming part of the sample-processing cartridge, and which are interchangeable between different sample-processing cartridges, along with timing information indicative of chemical processes and the different times and identification of the selected biological-sample stimulators of the plurality used for performing the analysis at the different times.

7. The analyzer apparatus of claim 1, wherein the sample-specific configuration circuitry is configured to instruct the selected biological-sample stimulators to emit the energy, thereby causing the biochemical processing of the biological sample contained within specific biochemical processing modules of the sample-processing cartridge based on parameters identified by the configuration information, the parameters including identified spatial locations of the biochemical processing modules, the selected biological-sample stimulators used to cause the biochemical processing of the biological sample within the biochemical processing modules, and corresponding times for emitting the energy.

8. The analyzer apparatus of claim 7, wherein the parameters include control instructions for the biological-sample stimulators to emit the energy including two-dimensional or three-dimensional locations associated with the sample-processing cartridge for emitting of the energy.

9. The analyzer apparatus of claim 1, further including:

the sample-processing cartridge comprising:

a base board with fluid chambers and channels configured and arranged for processing the biological sample therein;

a plurality of biochemical processing modules that are mounted on or are otherwise part of the base board, the plurality of biochemical processing modules each including a chamber and being in fluidic communication with the fluid chambers and channels of the base board; and the data indicative of the configuration of the sample-processing cartridge that is located on a surface of the sample-processing cartridge; and where the pneumatic stimulator including the pump, tubing and channels, is configured and arranged to control movement of the biological sample through the sample-processing cartridge based on the configuration information throughout the analysis.

10. The analyzer apparatus of claim 9, wherein the data includes a barcode or radio frequency tag on the sample-processing cartridge that stores the configuration information or identifies a memory location of the configuration information.

11. The analyzer apparatus of claim 10, wherein the data is indicative of a cloud-based memory location that is external to the analyzer apparatus or an internal memory location of a memory circuit located within the analyzer apparatus that provides the configuration information.

12. The analyzer apparatus of claim 1, wherein the gantry includes:

electrical circuitry configured and arranged to provide power and cause movement of the gantry head and a bridge framework;

a set of tracks configured and arranged parallel to one another;

the bridge framework that spans the set of tracks and is configured and arranged to travel along the set of tracks in a first direction that the set of tracks elongate in;

brackets that support the set of tracks and that are coupled to a frame of the container; and the gantry head that is supported by the bridge framework, the gantry head being configured and arranged to travel in a second direction that is perpendicular to the first direction and along the bridge framework, wherein the gantry head includes the plurality of interface tools arranged on the gantry head and configured and arranged to selectively emit the energy toward a plurality of locations associated with the sample-processing cartridge.

13. The analyzer apparatus of claim 12, wherein the gantry head is configured and arranged to physically move, via the electrical circuitry, the set of tracks, and the bridge framework, to different locations within the container and associated with the sample-processing cartridge.

14. The analyzer apparatus of claim 12, wherein the plurality of interface tools are located around a periphery of the gantry head and the gantry head and the electrical circuitry are configured and arranged to emit the energy towards the sample-processing cartridge by rotating the gantry head to align a respective interface tool with a particular location of the plurality of locations, and wherein the gantry head includes:
   the heat source or cooling source configured and arranged to heat and/or cool the biological sample;
   the magnet configured and arranged to apply magnetic forces;
   the motor configured and arranged to apply mechanical forces; and
   an acoustic tool configured and arranged to output sound waves.

15. The analyzer apparatus of claim 12, wherein the gantry head is arranged to detach from the bridge framework and the bridge framework is further configured and arranged to attach to another gantry head having a different set of interface tools than the gantry head.

16. The analyzer apparatus of claim 1, wherein the gantry head is configured and arranged to move in X, Y, and Z directions and to rotate.

17. The analyzer apparatus of claim 1, further including a bridge framework, and wherein the gantry includes:
   electrical circuitry configured and arranged to provide power and cause movement of the gantry head and the bridge framework;
   at least one track configured and arranged to facilitated movement of the bridge framework; and
   wherein the gantry head is further supported by the bridge framework, the gantry head being configured and arranged to travel in a direction that is orthogonal to a plane along which the at least one track is oriented.

18. A method of configuring an analyzer apparatus for performing a particular analysis on a biological sample, the method comprising:
   providing a sample-processing cartridge comprising a base board with fluid chambers, channels and a biological sample therein to an analyzer apparatus; and
   using sample-specific configuration circuitry of the analyzer apparatus to:
      identify configuration information specific to the sample-processing cartridge by scanning a location of the sample-processing cartridge, and
      configure the analyzer apparatus for a series of state configurations using the configuration information by:
         selecting which of a plurality of biological-sample stimulators of the analyzer apparatus to emit energy toward the sample-processing cartridge at plurality of different times specific to an analysis of the biological sample, the plurality of biological-sample stimulators being configured and arranged to emit energy, thereby causing physical interactions with the biological sample, wherein the plurality of biological-sample stimulators include:
            a gantry having a plurality of interface tools arranged about a gantry head, the plurality of interface tools including a magnet, a cooling source or heating source, and a motor, wherein the gantry head is movable in at least two-dimensional directions and is rotatable,
            a pneumatic stimulator including a pump, tubing and channels, and
            an optical stimulator, including a light source and a detector, including circuitry;
         identifying different positions in the analyzer apparatus for the gantry associated with at least a subset of the plurality of different times; and
         performing biochemical processing on the biological sample using the selected ones of the plurality of biological-sample stimulators at each of the plurality of different times.

19. The method of claim 18, wherein configuring the analyzer apparatus for the series of state configurations further includes:
   storing the configuration information on memory internal to the analyzer apparatus;
   providing spatial location information of specific biochemical processing modules forming part of the sample-processing cartridge, and which are interchangeable between different sample-processing cartridges, along with timing information indicative of chemical processes and the plurality of different times, and the identification of the selected biological-sample stimulators of the analyzer apparatus; and
   directing the selected biological-sample stimulators to emit the energy at the plurality of different times during the analysis based on the spatial location information of the biochemical processing modules.

* * * * *